(12) United States Patent
Heo et al.

(10) Patent No.: US 11,992,355 B2
(45) Date of Patent: May 28, 2024

(54) METHOD, APPARATUS, AND COMPUTER PROGRAM FOR PLANNING IMPLANT SURGERY

(71) Applicant: IMSOL CORP., Gyeonggi-do (KR)

(72) Inventors: Da Som Heo, Gyeonggi-do (KR); Yun Ho Lee, Gyeonggi-do (KR); Heui Jung Yang, Gyeonggi-do (KR)

(73) Assignee: IMSOL CORP. (KR)

( * ) Notice: Subject to any disclaimer, the term of this patent is extended or adjusted under 35 U.S.C. 154(b) by 699 days.

(21) Appl. No.: 16/778,922

(22) Filed: Jan. 31, 2020

(65) Prior Publication Data
US 2021/0030378 A1  Feb. 4, 2021

(30) Foreign Application Priority Data
Aug. 2, 2019 (KR) .......................... 10-2019-0094122

(51) Int. Cl.
*G06T 15/00* (2011.01)
*A61B 6/00* (2006.01)
(Continued)

(52) U.S. Cl.
CPC .............. *A61B 6/512* (2024.01); *A61B 6/032* (2013.01); *A61B 6/5229* (2013.01); *A61B 34/25* (2016.02); *A61C 1/084* (2013.01); *A61C 5/77* (2017.02); *A61C 9/0006* (2013.01); *A61C 9/004* (2013.01); *A61C 13/0004* (2013.01); *A61C 19/003* (2013.01); *A61B 2034/108* (2016.02); *A61B 2034/256* (2016.02); *A61B 2090/3912* (2016.02); *A61B 2090/3966* (2016.02)

(58) Field of Classification Search
USPC ......................................................... 345/418
See application file for complete search history.

(56) References Cited

U.S. PATENT DOCUMENTS 10,383,705 B2 * 8/2019 Shanjani ................ A61C 7/002
10,426,578 B2 * 10/2019 Rubbert ............... A61C 8/0012
(Continued)

OTHER PUBLICATIONS

BlueSky Bio, CBCT to Surgical Guide Training Video—Using the Impression Inversion Protocol, Jun. 1, 2017, https://www.youtube.com/watch?v=cw3fGjPckh4 (Year: 2017).*
(Continued)

*Primary Examiner* — Phu K Nguyen
(74) *Attorney, Agent, or Firm* — Quarles & Brady LLP

(57) ABSTRACT

Disclosed herein is a method of supporting implant surgery in a server, which includes obtaining a subject's oral CT image scanned with a guide model inserted into an oral cavity of the subject, the guide model being manufactured to a certain standard to group human teeth in any range so that the teeth belong to at least one group and to cover a tooth position of a corresponding group, the guide model including a marker made of a radiopaque or radiation semipermeable material, loading a library as information about the standard of the guide model, identifying the marker in the oral CT image, and generating a library matching CT image by matching the oral CT image with the library based on the marker included in the library and the marker identified in the oral CT image, and planning implant surgery of the subject using the library matching CT image.

28 Claims, 20 Drawing Sheets

(51) Int. Cl.
*A61B 6/03* (2006.01)
*A61B 6/51* (2024.01)
*A61B 34/00* (2016.01)
*A61C 1/08* (2006.01)
*A61C 5/77* (2017.01)
*A61C 9/00* (2006.01)
*A61C 13/00* (2006.01)
*A61C 13/15* (2006.01)
*A61B 34/10* (2016.01)
*A61B 90/00* (2016.01)

(56) References Cited

U.S. PATENT DOCUMENTS

| | | | | |
|---|---|---|---|---|
| 10,470,847 | B2* | 11/2019 | Shanjani | H04B 5/00 |
| 10,639,134 | B2* | 5/2020 | Shanjani | A61B 5/4542 |
| 11,059,107 | B2* | 7/2021 | Lee | A61C 1/084 |
| 11,219,506 | B2* | 1/2022 | Shanjani | A61C 19/045 |
| 2011/0045431 | A1* | 2/2011 | Groscurth | A61C 9/0053 |
| | | | | 433/74 |
| 2017/0079744 | A1* | 3/2017 | Scheffer | A61C 13/0003 |
| 2020/0205938 | A1* | 7/2020 | Lee | A61C 9/0046 |
| 2021/0030378 | A1* | 2/2021 | Heo | A61C 1/084 |

OTHER PUBLICATIONS

Bae MJ, Kim JY, Park JT, Cha JY, Kim HJ, Yu HS, Hwang CJ. Accuracy of miniscrew surgical guides assessed from cone-beam computed tomography and digital models. American Journal of Orthodontics and Dentofacial Orthopedics. Jun. 1, 2013;143(6):893-901.*

AD Surgical, Radiographic Dental Implant Surgical Guide Fabricate in 1 Minute with Termoplastic, Aug. 3, 2016, https://www.youtube.com/watch?v=Zy0zyYOnNsg.*

3Shape Training Videos, 3Shape Implant Studio—Guide Design—Part 2, Aug. 10, 2017, https://www.youtube.com/watch?v=llJt-wDI7BE.*

3Shape Training Videos, 3Shape Implant Studio—Guide Design—Part 1, Aug. 10, 2017, https://www.youtube.com/watch?v=cdmEGIMcRAE.*

Ramasamy M, Raja R, Narendrakumar R. Implant surgical guides: From the past to the present. Journal of pharmacy & bioallied sciences. Jun. 2013;5(Suppl 1):S98.*

Malara P, Dobrzański LB. Computer-aided design and manufacturing of dental surgical guides based on cone beam computed tomography. Archives of Materials Science and Engineering. Dec. 2015;76(2):140-9.*

Jones A. Accuracy of mucosa supported guided dental implant surgery. Clinical Case Reports. Nov. 1, 2018;6(11):2131-9.*

Savion, All on Six Implant with Surgical Guide by Dr. Ariel Savion, Nov. 2016, https://www.youtube.com/watch?v=vfxfJPspEzs.*

Neodent, EasyGuide Surgical Manual, A Straumann group branch, pp. 1-28, 2021.*

Biohorizons, Guided Surgery Kit Catalog and Manual, Nov. 2013.*

\* cited by examiner

METHOD, APPARATUS, AND COMPUTER PROGRAM FOR PLANNING IMPLANT SURGERY

CROSS-REFERENCE TO RELATED APPLICATIONS

This application claims priority to and the benefit of Korean Patent Application No. 10-2019-0094122 filed on Aug. 2, 2019, the disclosure of which is incorporated herein by reference in its entirety.

BACKGROUND OF THE INVENTION

Field of the Invention

The present invention relates to a computer program for planning dental implant surgery and for designing an implant surgical guide according to the surgical plan. More specifically, the present invention relates to a method, an apparatus, and a computer program for reducing a preparation time for surgery by planning implant surgery using a guide stent that is produced in advance to a certain standard.

Description of the Related Art

Dental implant surgery involves placing an implant fixture in an alveolar bone. A guide instrument, commonly called a guide stent or a surgical guide, is used to properly place the implant fixture in the alveolar bone.

The guide stent currently used in the field of surgery is manufactured by a method similar to that disclosed in Korean Patent No. 10-1473192 (Prior Document 1), entitled "Method of Manufacturing Implant Guide Stent", published on Dec. 16, 2014, Korean Patent No. 10-1554157 (Prior Document 2), entitled "Reference Marker for Intra-Oral Attachment and Method of Manufacturing Guide Stent for Implant Surgery Using the Same, published on Sep. 21, 2015, or the like.

The method of manufacturing a guide stent, which is disclosed in Prior Document 2, is illustrated in FIG. 1A of the present specification, and a brief description of the conventional method of manufacturing a guide stent with reference to FIG. 1A is as follows. First, at a dental clinic, a practitioner obtains a three-dimensional image inside a subject's oral cavity (intra-oral periodontal tissue) through a CT scan, and obtains a three-dimensional external shape image corresponding to the three-dimensional image through an oral scan (s1). The CT scan can check only a hard tissue inside the oral cavity, which is necessary to check the shape of a subject's gum or tooth crown. On the other hand, the oral scan is performed by inserting a scanner into the subject's oral cavity by the practitioner, which causes frequent image distortion because the scan must be performed along the inside of the oral cavity.

The three-dimensional image inside the subject's oral cavity and the external shape image, which are obtained in this manner, are matched with each other based on the characteristic or marker of the tooth included in each of the images, and a three-dimensional surgical guide image is generated through the image matching (s2). The practitioner plans implant surgery using the three-dimensional surgical guide image (s3), and a guide stent formed with a guide hole is manufactured according to the surgical guide image.

Typically, it takes about 2 to 3 days to perform the first step s1 to the last step s4. This is because the guide stent is not manufactured at the dental clinic, but is manufactured by an external company with precision machining equipment. That is, since the practitioner receives the guide stent after the patient takes the CT scan and oral scanning at the dental clinic and the guide stent manufacturer manufactures the guide stent by generating the three-dimensional surgical guide image or planning the implant surgery, it may take a lot of time to prepare for surgery. In addition, since the intra-oral image obtained through the oral scan has distortion, the guide stent produced through the image matching may not exactly fit the oral structure of the subject in some cases.

Meanwhile, the guide stent is sometimes manufactured using equipment such as a 3D printer provided at the dental clinic. However, even in this case, 3D printing takes a lot of time. In addition, when the 3D printer is used, the guide stent is made of a soft material, in which case a separate metal member is mounted to a hole in which an implant sleeve is placed in the guide stent. However, when the guide stent made of the soft material is twisted in the process of mounting the metal member to the guide hole, an error may occur when the completed guide stent is mounted to the patient.

SUMMARY OF THE INVENTION

The present invention has been made in view of the above-mentioned problem, and it is an object of the present invention to shorten a preparation time for implant surgery using a guide stent that is produced in advance to a certain standard. More specifically, it is an object of the present invention to shorten a preparation time for surgery by planning implant surgery using a standardized guide stent and machining the standardized guide stent according to the surgical plan, rather than manufacturing a separate guide stent based on a patient's oral image as in the related art.

In addition, it is an object of the present invention to provide a surgical guide that is stably mounted into a subject's oral cavity without an error and designed to show an implant placement position and angle during surgery.

BRIEF DESCRIPTION OF THE DRAWINGS

FIG. 2 is a view for explaining a preguide device according to the embodiment of the present invention.

DETAILED DESCRIPTION OF THE PREFERRED EMBODIMENTS

Figure 1A:
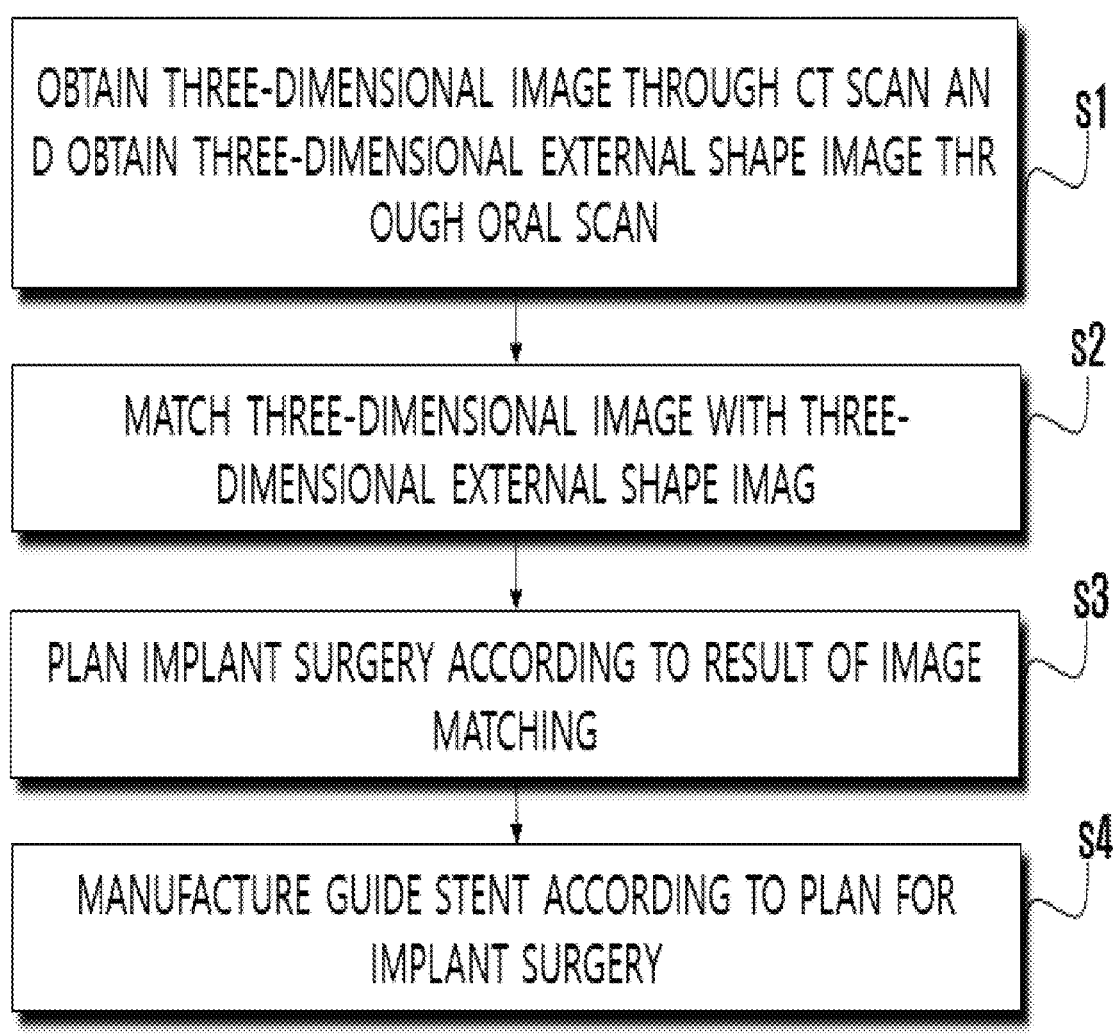
FIG. 1A is a flowchart for explaining a conventional method of manufacturing an implant guide stent.

The above objects, features and advantages will be described in detail with reference to the accompanying drawings, whereby those skilled in the art may easily implement the technical idea of the present invention. In certain embodiments, detailed descriptions of technology well known in the art will be omitted to avoid obscuring appreciation of the invention. Reference will now be made in detail to exemplary embodiments of the present invention, examples of which are illustrated in the accompanying drawings. In the drawings, like reference numerals are used to indicate the same or like components, all combinations described in the specification and claims may be combined in any way. As used in the invention and the appended claims, the singular forms "a", "an" and "the" are intended to include the plural forms as well, unless context clearly indicates otherwise.

Figure 1B:
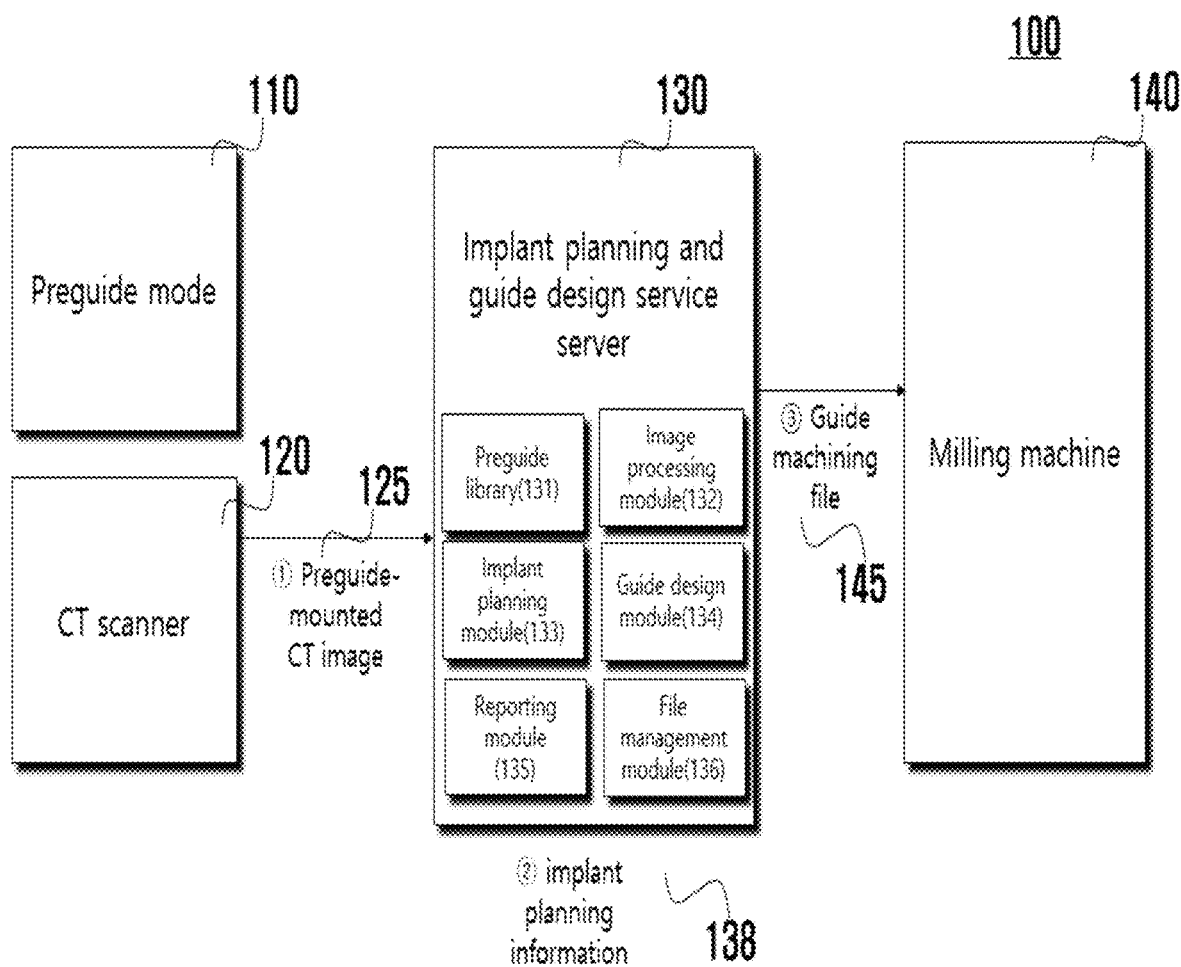
FIG. 1B is a diagram for explaining a configuration of an implant surgical planning system according to an embodiment of the present invention.

FIG. 1B is a diagram for explaining a configuration of an implant surgical planning system 100 according to an embodiment of the present invention.

As illustrated in FIG. 1B, the implant planning system according to the embodiment of the present invention may include a guide stent set 110 produced in advance to a certain standard, a CT image scanner 120, a service server 130 for performing an implant surgical planning and guide design function, and a milling machine 140 for machining a guide stent.

Meanwhile, although the CT scanner 120, the guide design service server 130, and the milling machine 140 are illustrated as being separate independent devices in FIG. 1B, this is merely an example. The implant planning system according to the embodiment of the present invention refers to an apparatus or a combination of apparatuses for performing a CT image scanning function, an implant planning and guide design function, and/or a guide milling function, each of which may be implemented by independent hardware or cloud-based software or may be implemented by integrally-formed software and hardware. For example, the implant planning and guide design service function 130 according to the embodiment of the present invention may be implemented by software, and the software may be installed in a general-purpose server for execution.

The guide stent set 110 according to the embodiment of the present invention is not manufactured separately based on the patient's oral image, but is a ready-made product produced in advance to a certain standard according to the implant placement position. The guide stent set 110 may function as a surgical guide that is applicable to surgery of a corresponding patient through a predetermined process in the milling machine 140 according to the design of the implant planning service server. In the present specification, the guide stent before being machined is referred to as a preguide.

The preguide set according to the embodiment of the present invention will be described with reference to FIG. 2. FIG. 2 is a view for explaining a preguide device according to the embodiment of the present invention.

Figure 2A:
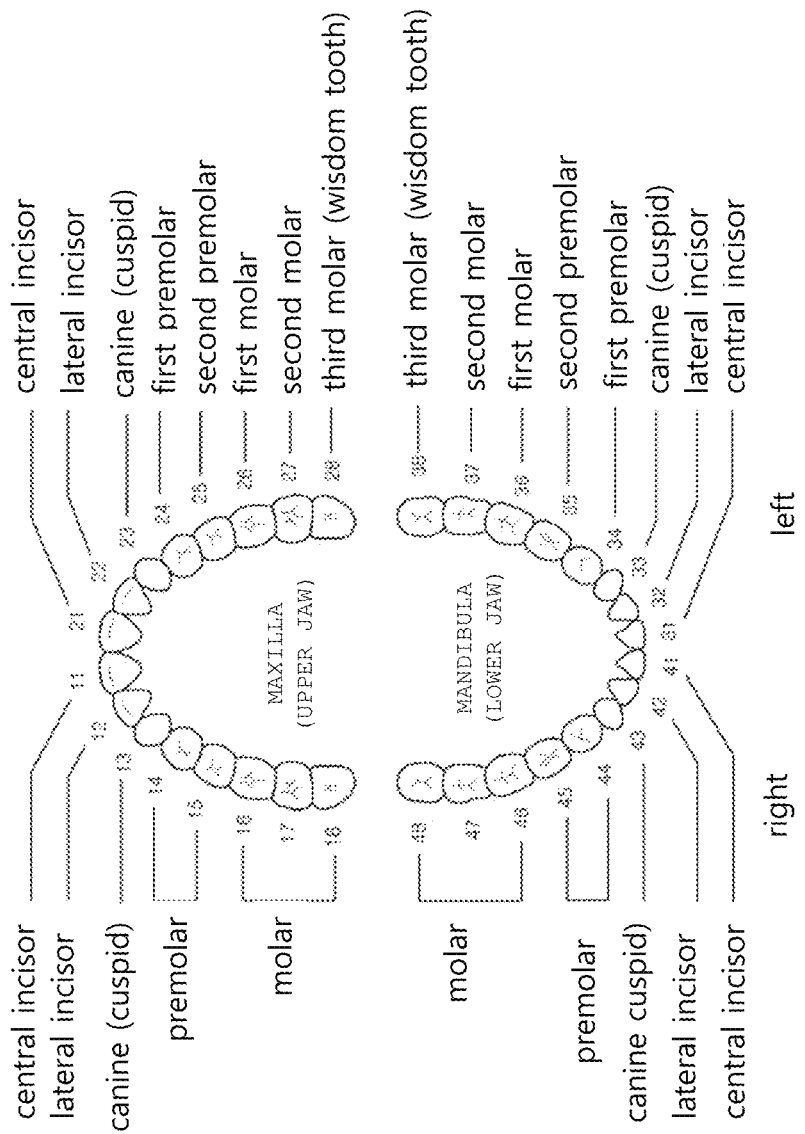
FIG. 2A is a view for explaining the human teeth

According to the embodiment of the present invention, the preguide may be formed of a maxillary (upper jaw) model and a mandibular (lower jaw) model according to the implant placement position. For example, when human teeth are numbered as illustrated in FIG. 2A, the preguide set according to the embodiment of the present invention may include at least one maxillary model formed to group maxillary teeth in any range such as maxillae 18-14, 16-22, 15-25, 28-24, and 26-11 and to cover the position of the tooth of the corresponding group. In addition, the preguide set may include at least one mandibular model formed to group mandibular teeth in any range such as mandibulae 48-43, 46-31, 45-35, 38-34, and 36-42 and to cover the position of the tooth of the corresponding group.

Figure 2B:
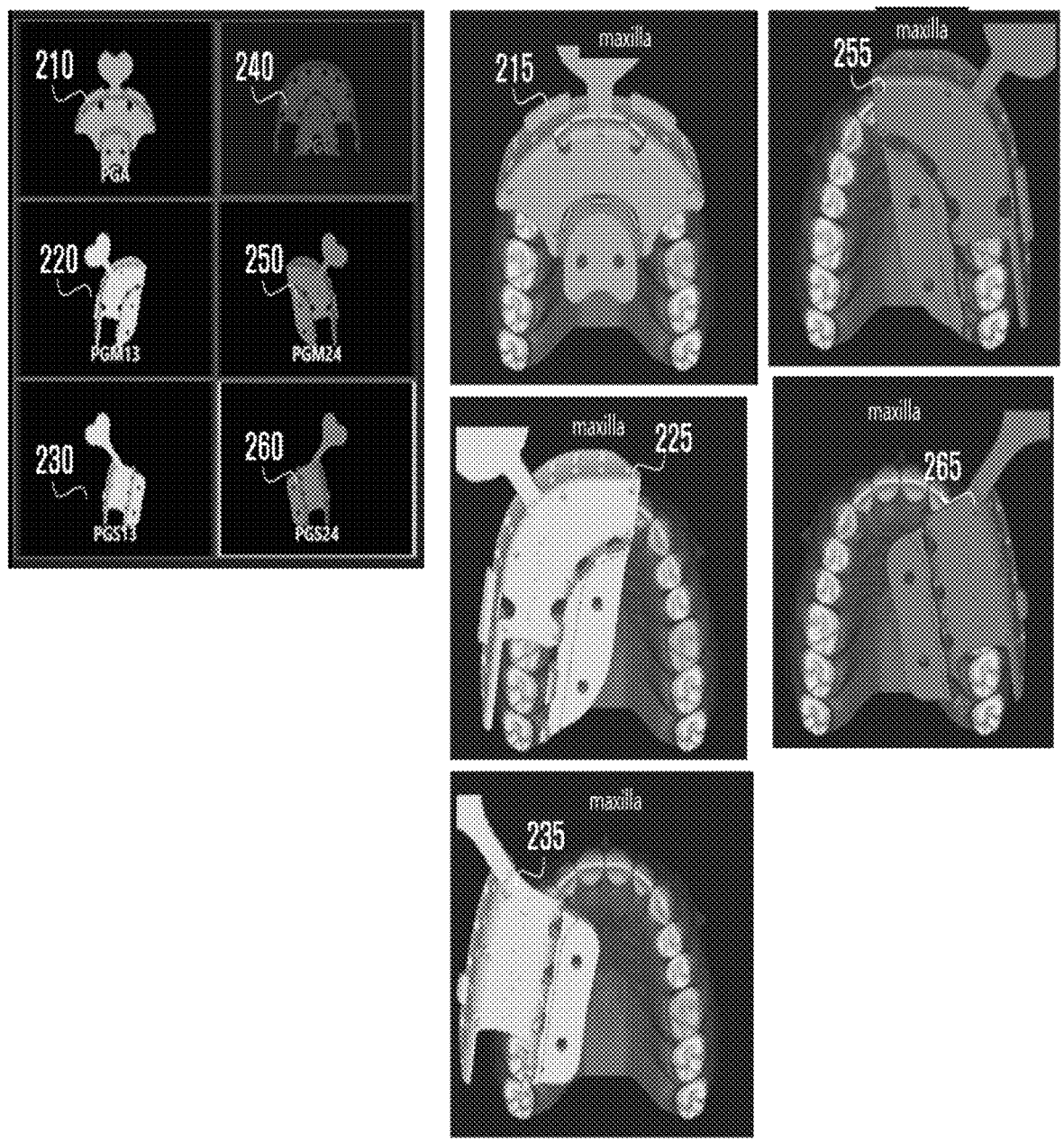
FIG. 2B is a view for explaining a preguide device according to the embodiment of the present invention.

For example, the maxillary model may be formed in a shape such as reference numeral 210, 220, 230, 240, 250, or 260 of FIG. 2B, and reference numerals 215, 225, 235, 255, and 265 of FIG. 2B illustrate respective examples in which the preguide maxillary models designated by reference numerals 210, 220, 230, 250, and 260 are mounted in the oral cavity.

Figure 2C:
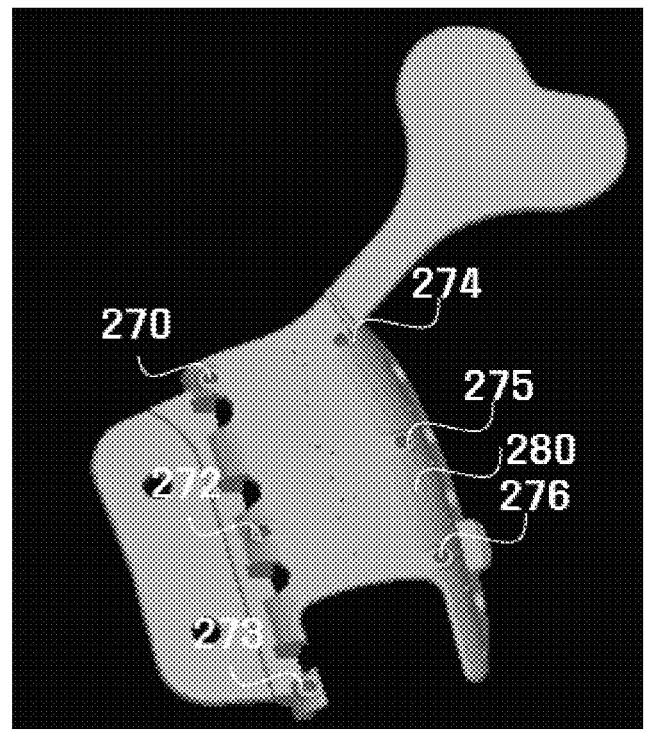
FIG. 2C is a view for explaining the position of the marker in the pre-guide device according to the embodiment of the pre sent invention

Meanwhile, the preguide according to the embodiment of the present invention may include a guide tray designated by reference numeral 280 of FIG. 2C, an impression material such as resin formed in the guide tray to obtain an impression inside the oral cavity, and one or more markers 270 to 276 made of a radiopaque material. In addition, the preguide according to the embodiment of the present invention may also have a vinyl film formed on its one surface on which the tooth is molded in a pattern form by the impression material such as resin.

According to the embodiment of the present invention, a model, which covers a position to be implanted, of the preguide set is applied to a mouth of a subject and an implant placement region is molded in a pattern form through the impression material. That is, the implant placement region of the subject is molded in the pattern form in the impression material of the preguide. For example, when the impression material is resin, the impression material may be cured through photopolymerization or self-polymerization. In this case, since the preguide according to the embodiment of the present invention has the vinyl film formed on its surface on which the implant placement region of the subject is molded in the pattern form by the impression material, the preguide may be easily detached from the oral cavity even when the impression material is cured through photopolymerization or self-polymerization. Furthermore, according to the embodiment of the present invention, the impression material is suitable to be cured in the oral cavity to prevent the shrinkage of the preguide.

The subject's oral pattern obtained by the preguide is intactly formed in the surgical guide that is finally completed by machining the preguide 110 in the milling machine 140 according to the embodiment of the present invention. Therefore, the subject's oral pattern may be used as a means for physically matching the surgical guide with the implant placement region of the subject. In other words, since the implant placement region is molded in the pattern form in the impression resin included in the preguide according to the embodiment of the present invention and the impression resin molded in the pattern form is then included in the surgical guide completed by machining the preguide, the preguide may function as a specific implant-specific surgical guide for the subject even though the preguide is a ready-made product.

Meanwhile, the oral image is scanned by the CT scanner 120 while the preguide is applied to the mouth of the subject. The markers 270 to 276 may be displayed on a three-dimensional image obtained through CT scanning because they are a radiopaque or radiation semipermeable material. The markers displayed on the CT image may be used as matching reference of the preguide image in the process of processing the CT image.

In addition, the preguide according to the embodiment of the present invention is machined into the surgical guide in the milling machine 140 as described above, in which case a jig holder may be formed on one surface of the preguide so as to be physically coupled to the jig of the milling machine so that the preguide may be accurately positioned and machined at a preset coordinate by the milling machine 140.

Figure 2D:
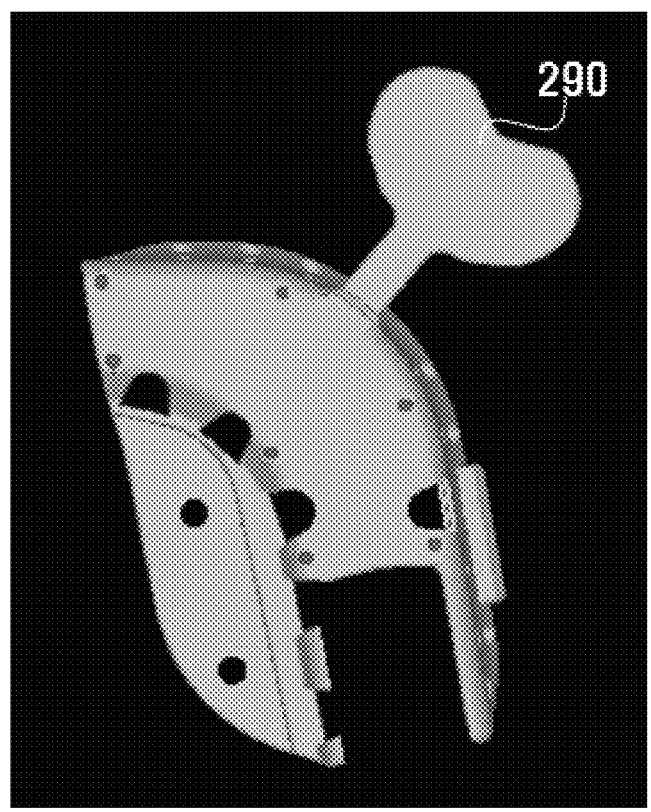
FIG. 2D is a view for explaining the position of the marker in the guide device according to another embodiment of the pre sent invention

It should be noted that the preguide model illustrated in FIGS. 2B to 2D is an example in the present specification and the present invention is not limited thereto. That is, the preguide device according to the embodiment of the present invention is a ready-made product produced in advance to a certain standard according to the position to be implanted, and includes an impression material that may be used to mold the implant placement region in a pattern form and a marker that may be displayed on the CT image, but is not limited thereto. For example, the marker may not be formed at the positions 270 to 276 illustrated in FIG. 2C, but may be formed at the handle 290 of FIG. 2D or preferably at three or more positions from among the positions 270 to 276 of FIG. 2C. According to a further embodiment of the present invention, the marker is used as a reference for matching the preguide library with the preguide image. Therefore, it should be noted that the marker may be formed of a point, a line, a plane, etc., so as to be used as a matching reference, and the present invention may not be interpreted as being limited to the shape of the marker.

Returning to the description of FIG. 1 again, the CT scanner 120 may scan the CT image of the preguide 110 inserted into the oral cavity of the subject, and the implant planning server 130 may receive the CT image generated by the CT scanner 120 (see reference numeral 125 of FIG. 1).

The implant planning and guide design service server 130 according to the embodiment of the present invention may include a preguide library 131, an image processing module 132, an implant planning module 133, a guide design module 134, a reporting module, and a file management module 136.

Although not separately illustrated in FIG. 1B, the preguide library 131 may be stored in a storage unit of the service server 130. The preguide library 131 is a database for a set of information about the preguide 110 and may include information about the shape, size, image, and material of the preguide, and about the position of a marker of a corresponding model. For example, when the preguide model mounted to the subject is identified through the CT image or through the user input, the service server 130 may load the data of the model from the preguide library 131.

The image processing module 132 may perform a function of matching the CT image 125 with the loaded preguide data. The intra-oral image 125 obtained through the CT scanning may include information about internal tissues, such as the crown (the upper part of the tooth appearing outside the gum), the tooth root (the lower part of the tooth hidden inside the gum as the part coupled to the alveolar bone), and the alveolar bone within the oral cavity, and may include a marker image of the preguide 110. The image processing module 132 may match the data of the preguide library to the CT image based on the marker image.

The CT image does not provide accurate information about the gum. Accordingly, in order to solve this problem in the related art, a three-dimensional external shape image is obtained through an oral scan and the external shape image is matched with a three-dimensional image inside an oral cavity. However, the embodiment of the present invention does not require a separate oral scan. This is because the preguide 110 according to the embodiment of the present invention is a standard product, the information about the shape thereof is prestored in the planning server 130 as the data of the preguide library 131, and the image processing module 132 may match the preguide library 131 to the CT image 125 based on the marker. A more detailed description related to matching the preguide library data with the CT image according to the embodiment of the present invention will be given later with reference to FIGS. 6 to 7.

In addition, the image processing module 132 may perform a function of segmenting the maxillary image and the mandibular image in the CT image. The CT image according to the embodiment of the present invention is obtained with the maxilla and the mandibula open as much as the thickness of the preguide because it is scanned with the subject biting the preguide 110 with his/her mouth. Thus, the image processing module 132 may perform a function of correcting an error due to the thickness of the preguide by separating the maxillary image and the mandibular image based on an arbitrary line and reconstructing the separated maxillary image and mandibular image for occlusion.

Figure 10:
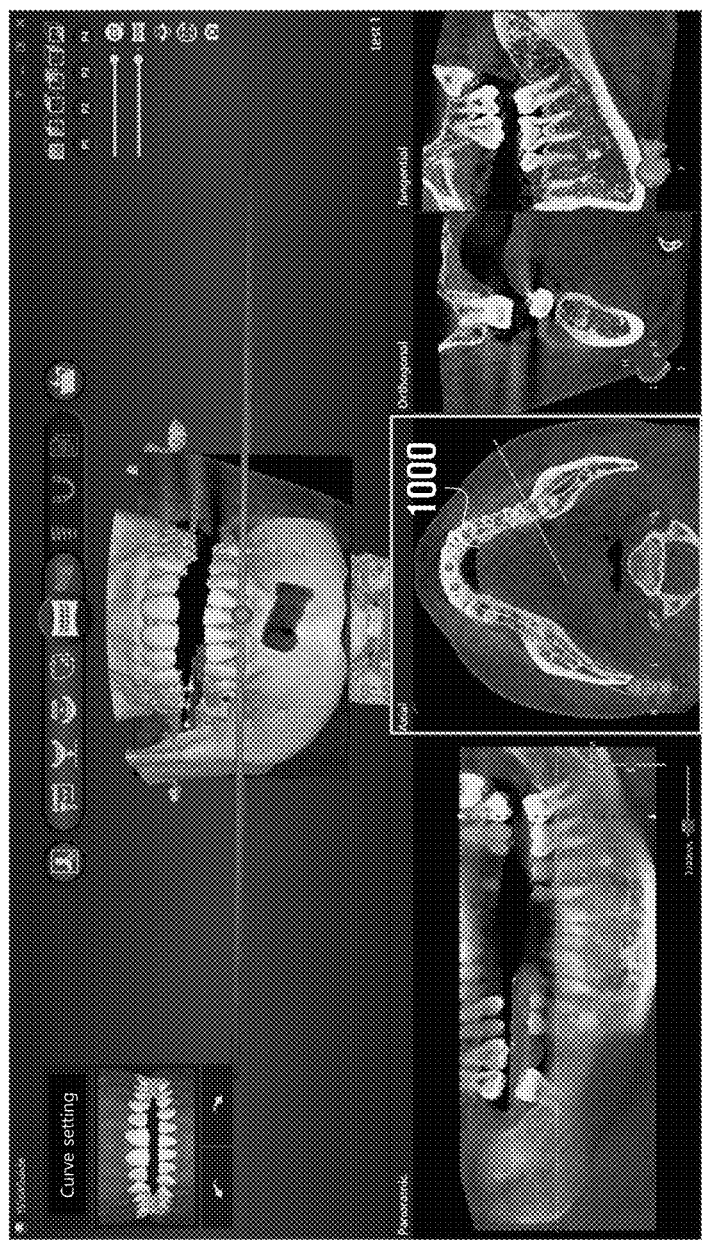
FIG. 10 is a view for explaining an example of a user interface for setting an oral curve to generate a panoramic image in the implant planning service server according to the embodiment of the present invention.
Figure 11:
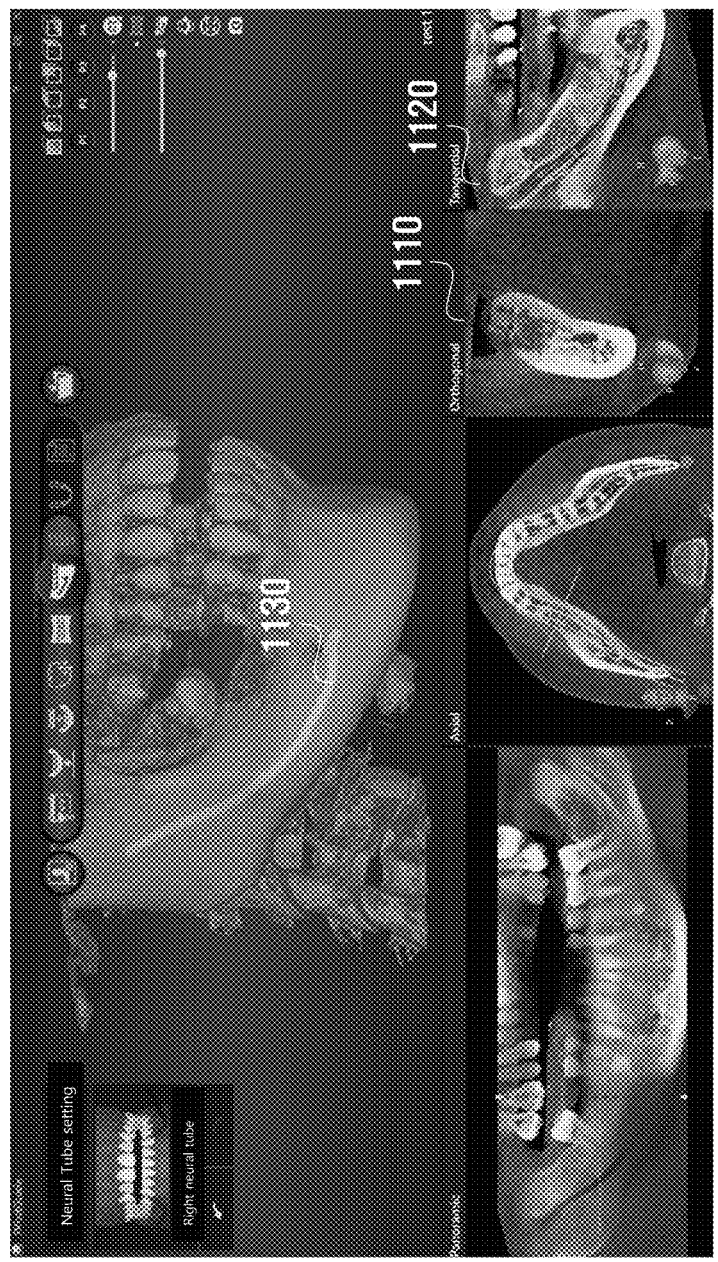
FIG. 11 is a view for explaining an example of a user interface for setting a mandibular neural tube in the implant planning service server according to the embodiment of the present invention.

Furthermore, the image processing module 132 may perform a function of displaying a tooth curve and a neural tube position on the corrected CT image. The image processing module 132 may perform a function of separating the maxillary and mandibular images to correct them for occlusion and recording information about the tooth curve and the neural tube position. A more detailed description related to adding data to the CT image will be given later with reference to FIGS. 8, 10, and 11.

The implant planning module 133 may perform a function of planning implant placement by setting the position and/or direction of the implant using the CT image processed by the image processing module 132. For example, the implant planning module 133 may place a crown object at the implant placement region by setting the angle and size of the crown object in the CT image. Then, the implant planning module 133 may place an implant object at a certain distance from the placed crown object. In addition, implant surgery may be planned by setting the size, length, position, and placement angle of the implant object. The information about the plan for implant surgery generated by the implant planning module 133 may be stored as implant planning information 138 and provided to the practitioner in the reporting module 135.

Particularly, the implant planning module 133 may perform a function of providing a guide to the practitioner while placing the implant object. For example, the implant planning module may provide a guide to position the implant at a depth of 0.5 to 1 mm from the bone, or may provide a guide to secure a distance of 2 mm or more between the implant and the root of the adjacent tooth. In addition, the implant planning module may provide a guide to secure a distance of 3 mm or more between the implant and the nerve, or may provide a guide to secure a distance of 2 mm or more between the implant and the sinus. Furthermore, the implant planning module may provide a guide such that the axis of the implant coincides with the center of the prosthesis, or may provide a guide to check whether the bone is sufficient at the implant placement position. As another example, the implant planning module may provide a guide to check whether the sleeve invades the tooth or the gum.

Furthermore, the implant planning module 133 may perform a function of setting an insertion direction of an implant surgical instrument, i.e., of a handpiece, together with an implant placement plan.

The guide design module 134 may perform a function of generating machining information of the preguide 110 according to the implant placement plan set by the implant planning module 133. For example, the guide design module 134 may set a guide hole region to be etched in the preguide by applying an offset in a preset range based on the type, size, and/or length of the implant sleeve determined by the implant planning module 133. In addition, the guide design module 134 may apply the insertion angle and position information of the implant surgical instrument, i.e., of the handpiece in the preguide to set a flat surface etching region at the upper portion of the preguide for the insertion of the handpiece.

The machining information of the preguide, i.e., the information about the guide hole region and/or the handpiece insertion region, generated by the guide design module 134 may be provided to the milling machine 140 in the form of a guide machining file 145, and the milling machine 140 may machine the preguide with reference to the machining file. For example, the milling machine 140 may generate a surgical guide for implant surgery by etching the depth and diameter region of the guide hole and the handpiece insertion region recorded in the machining file in the corresponding preguide.

Particularly, according to the embodiment of the present invention, the preguide machining information may include guide hole depth information. If there is no guide hole depth information, the milling machine 140 operates for a certain time even after the guide hole is etched in the preguide by the milling machine 140. However, according to the embodiment of the present invention, since the guide hole depth information is reflected, the time required to machine the preguide into the surgical guide in the milling machine 140 may be shortened. To this end, the guide design module according to the embodiment of the present invention may display a user interface as illustrated in FIG. 14.

Figure 14:
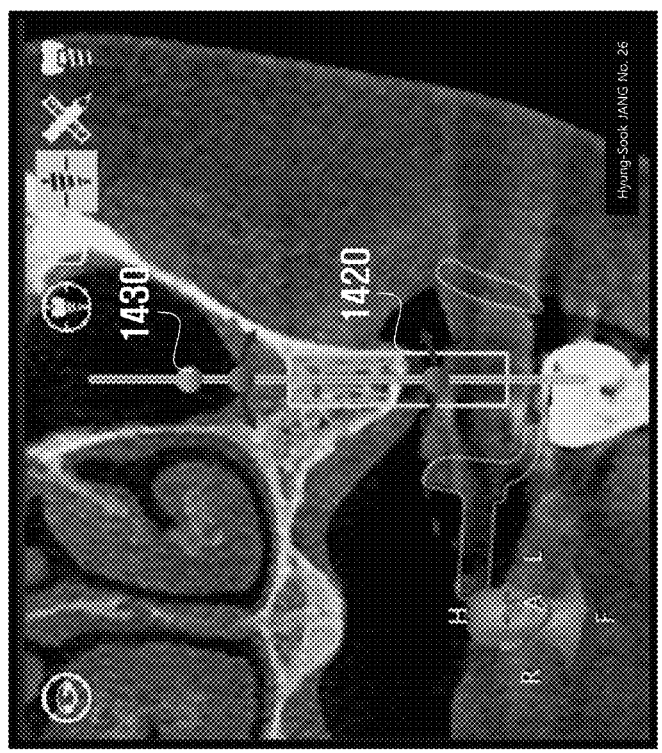
FIG. 14 is a view for explaining an example of a user interface for setting an etching depth of the preguide in the implant planning service server according to the embodiment of the present invention.

FIG. 14 illustrates an example of the user interface for setting the etching depth of the preguide in the implant planning service server according to the embodiment of the present invention.

In FIG. 14, reference numeral 1410 refers to a region indicative of an implant object and reference numeral 1420 refers to a guide hole etching region. For example, on the screen as illustrated in FIG. 14, the user may set the length of the guide hole object 1420 using a pointer object 1430. When the length of the guide hole object is determined, guide hole etching depth information may be generated by reflecting the same. Meanwhile, the reporting module 135 of the service server 130 may perform a function of providing the practitioner with the information about the CT image processed by the image processing module 132 and the type, size, position, and/or direction of the implant set by the implant planning module 133. In addition, the reporting module 135 may perform a function of analyzing the CT image to generate information about the subject's bone density, the distance between the implant placement position and the neural tube, etc., and of providing the information to the practitioner.

The file management module 136 may perform a function of reading and writing a file required for the implant surgical planning system 100 according to the embodiment of the present invention. More specifically, the file management module 136 may perform a function of executing and storing a CT image file generated by the CT scanner 120, a file recording the implant planning and guide design information generated by the service server 130, and/or a file required to operate the milling machine 140.

For example, when the format of the preguide-mounted CT image file 125 generated by the CT scanner is a DICOM file, the file management module 136 may perform a function of loading the file in the service server 130. In addition, the file management module 136 may process the CT image based on the loaded DICOM file and generate the implant planning data, generated based on the processed CT image, in an STL & XML file format. Furthermore, the file management module 136 may convert the STL file into an NC file for loading on the milling machine 140. The NC file may include milling position coordinate information.

Figure 3:
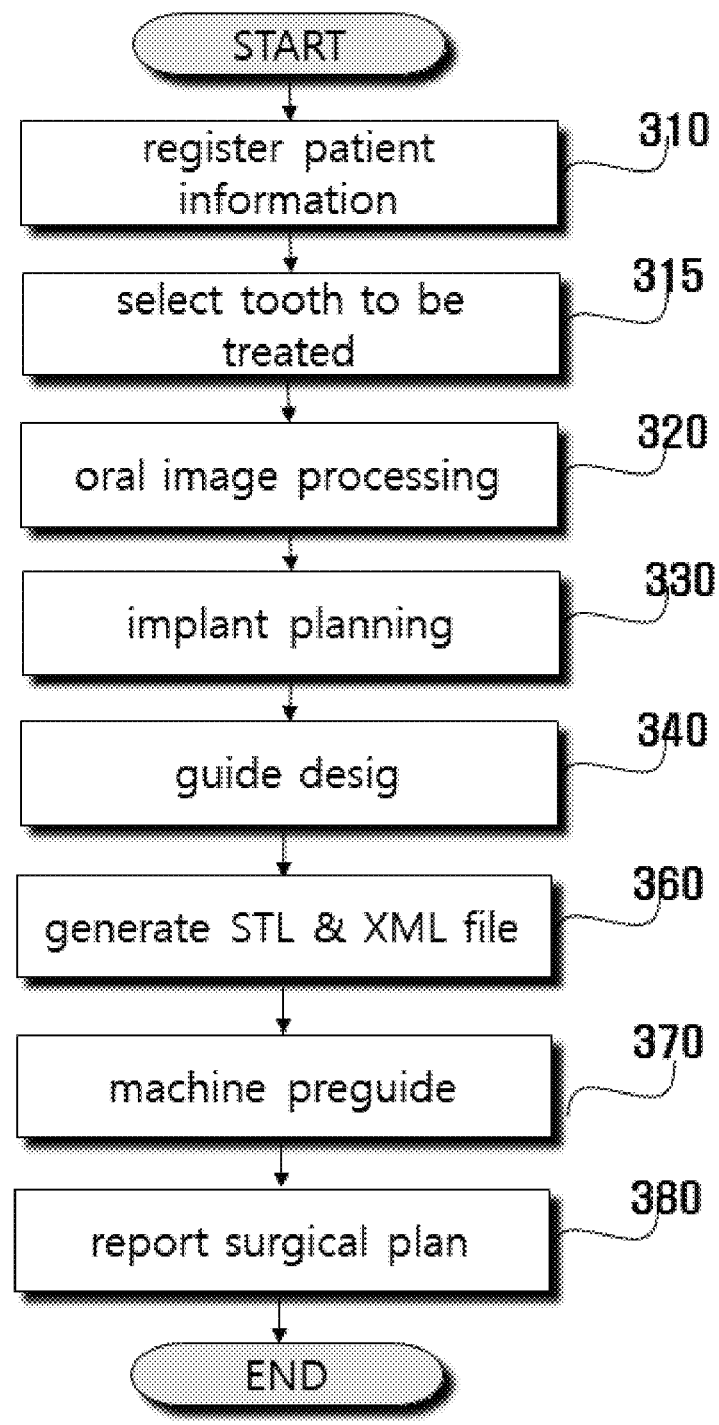
FIG. 3 is a flowchart for explaining a process of planning implant surgery and thus machining a surgical guide according to the embodiment of the present invention.

FIG. 3 is a flowchart for explaining a process of planning the implant surgery and thus generating the surgical guide by machining the preguide in the implant surgical planning system 100 according to the embodiment of the present invention.

Figure 6A:
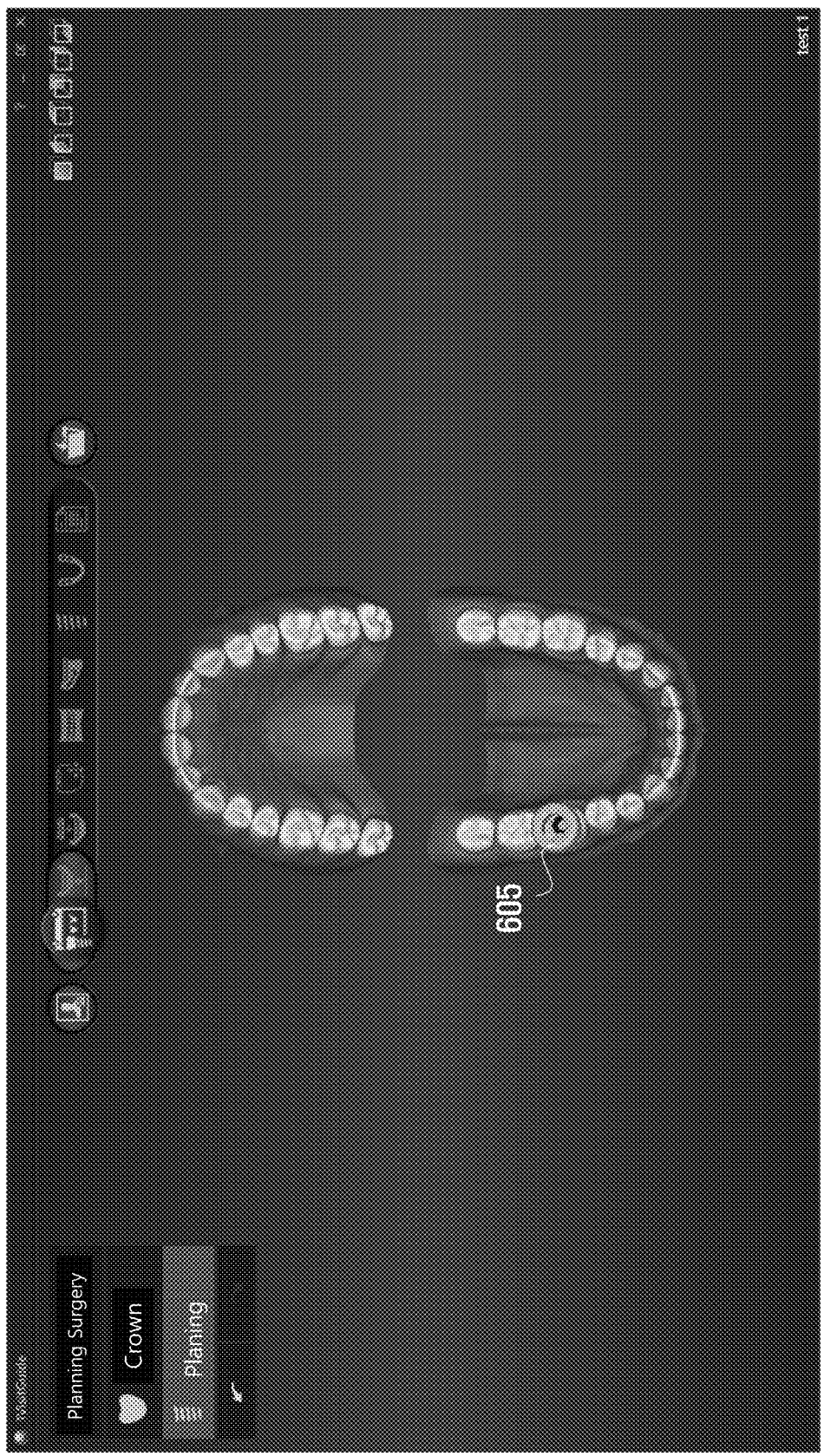
FIG. 6A is a view for explaining an example of a user interface for selecting a tooth to be treated in an implant planning service server according to the embodiment of the present invention.

In step 310, the implant planning system 100 may register information of patients who are subjects while planning an implant for a corresponding patient. In addition, the planning system may check a tooth to be treated of all human teeth (step 315). In this case, as illustrated in FIG. 6A, the planning system may display an image of all human teeth and the practitioner may obtain tooth information to be treated by selecting a tooth to be treated 605 of them.

Then, the implant planning system 100 may process a subject's oral image (step 320). More specifically, the practitioner may scan a CT image while a preguide device produced in advance to a certain standard by matching an implant placement position is applied to the mouth of the subject. The planning system may obtain a preguide-mounted CT image and match the CT image with a preguide library based on the image of a marker included in the preguide device in the CT image. A more detailed description of step 320 will be given later with reference to FIG. 4.

Figure 4:
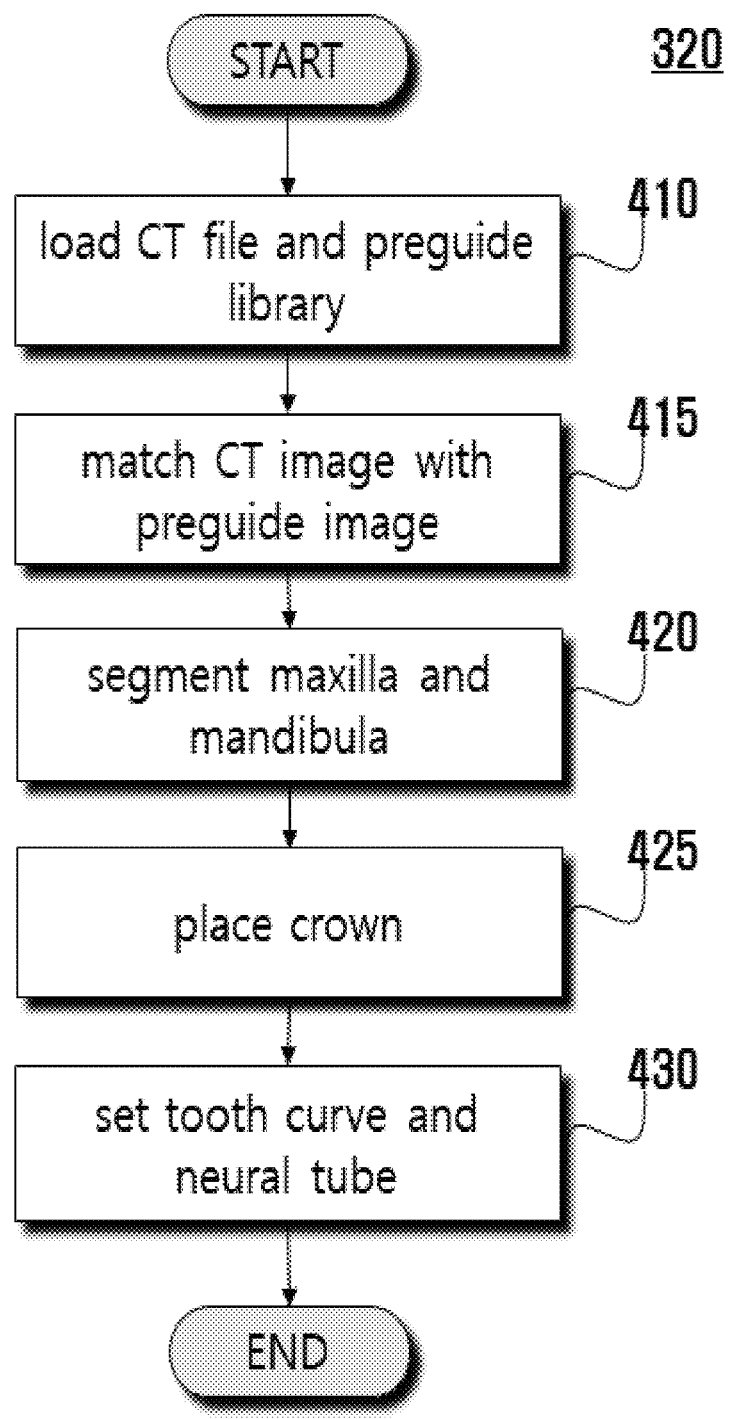
FIG. 4 is a flowchart for explaining a process of processing a subject's oral image according to the embodiment of the present invention.

FIG. 4 is a flowchart for explaining a detailed process of step 320 of FIG. 3 of processing the subject's oral image according to the embodiment of the present invention.

Figure 6B:
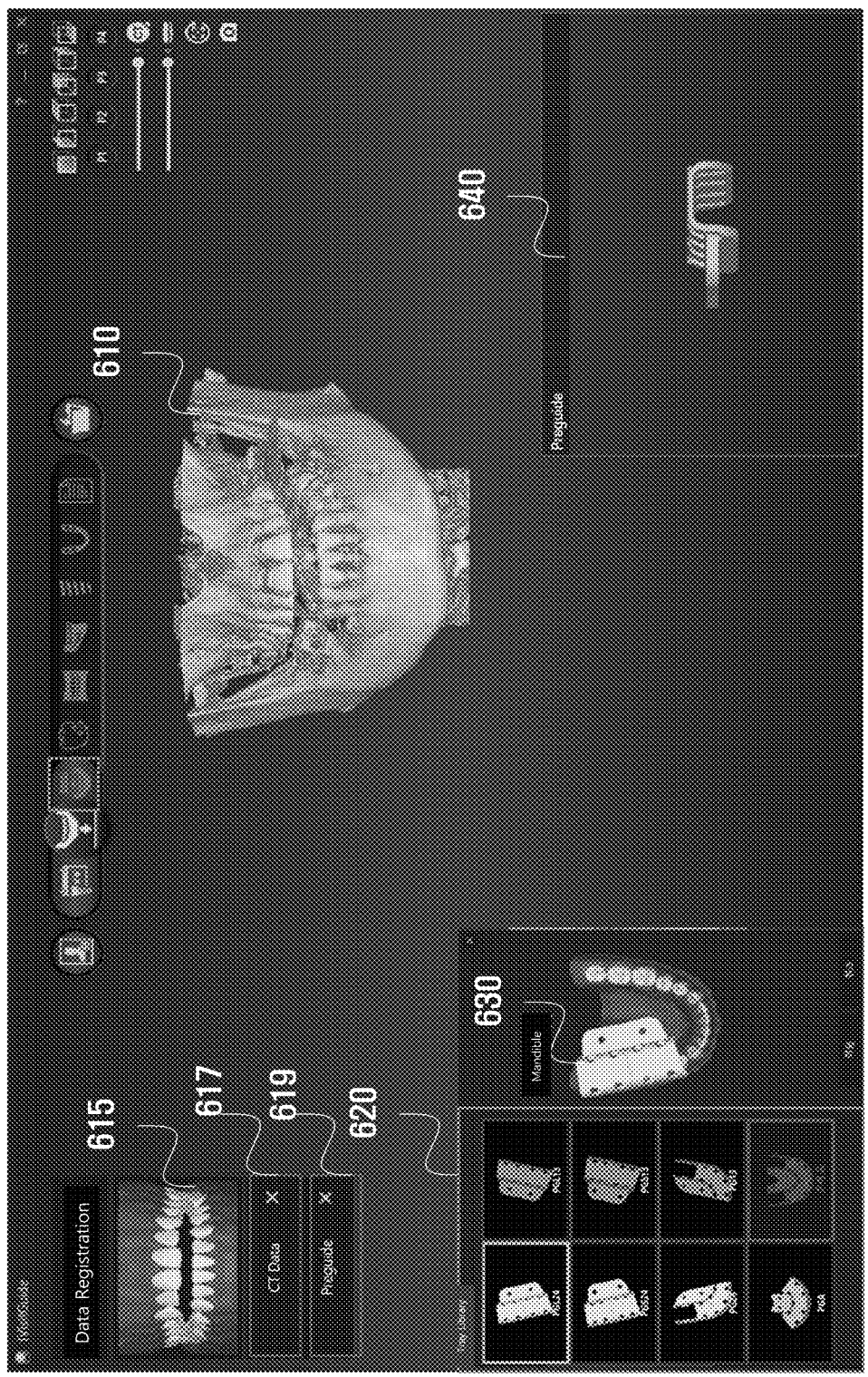
FIG. 6B is a view for explaining an example of a user interface for loading a CT image and a surgical guide library in an implant planning service server according to the embodiment of the present invention.

The implant planning system 100 may load the preguide-mounted CT image and a library for the preguide (step 410). In this case, the implant planning system may display a user interface as in the example of FIG. 6B. FIG. 6B illustrates an example of the user interface for loading the CT image and the preguide library.

In FIG. 6B, reference numeral 615 refers to a region indicative of a position of a tooth to be implanted, reference numerals 617 and 619 refer to user selection regions, and reference numerals 630 and 640 refer to preguide library regions indicative of information about the preguide. According to the embodiment of the present invention, when the user selects an object 617, the CT image may be displayed as in reference numeral 610. In addition, when the user selects an object 619, the preguide region may be displayed as in reference numeral 620 and the practitioner may select a preguide model mounted to the subject from reference numeral 620. For example, when the user selects an arbitrary preguide, the preguide may be displayed in the form in which it is mounted to the oral cavity as in reference numeral 630 and the three-dimensional image of the preguide may be displayed as in reference numeral 640.

Figure 7:
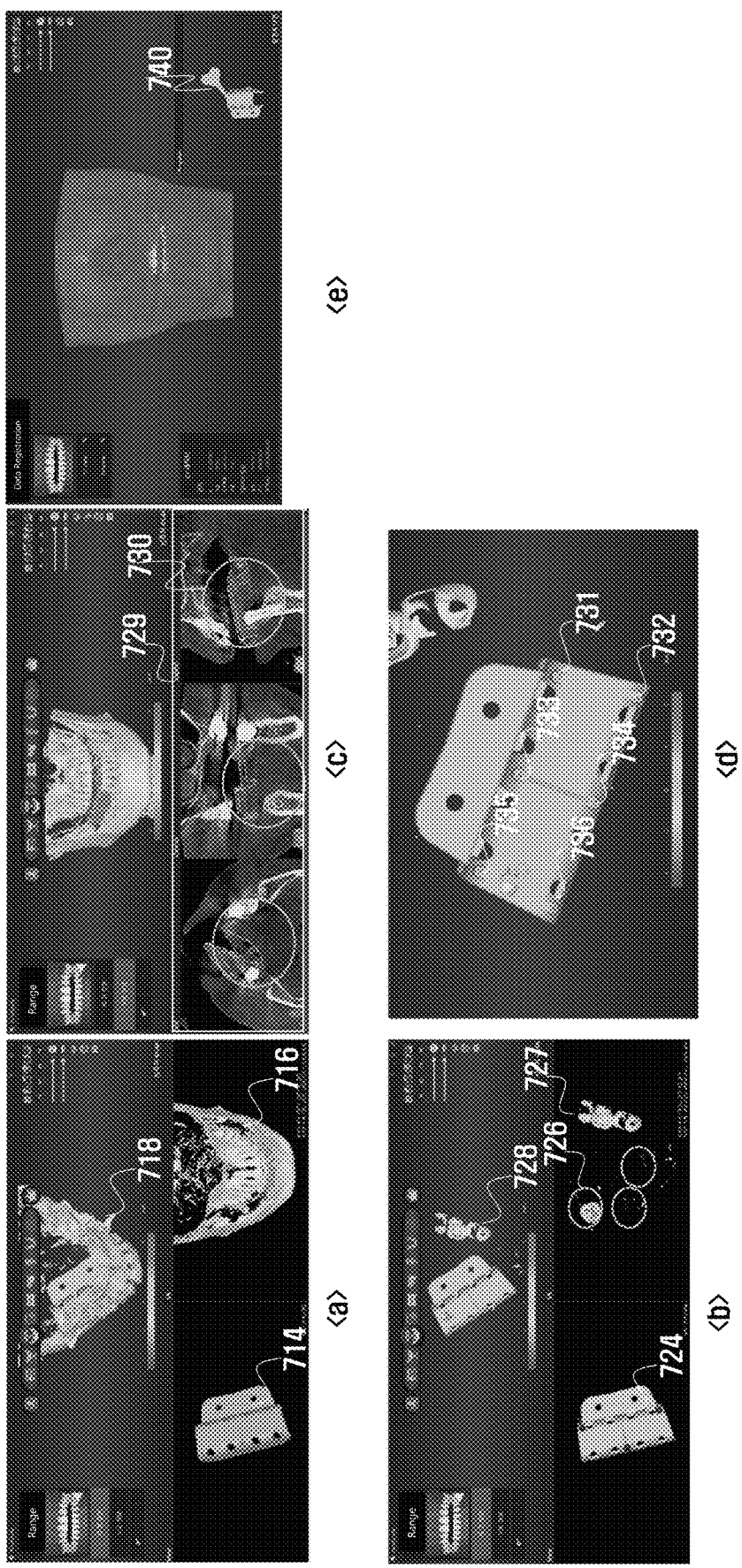
FIG. 7 is a view for explaining an example of a user interface for matching a CT image with a surgical guide library in the implant planning service server according to the embodiment of the present invention.

Returning to the description of FIG. 4 again, the implant planning system 100 may match the CT image with the preguide image in step 415. In this case, the implant planning system may display a user interface as in the example of FIG. 7. FIG. 7 is a view for explaining an example of the user interface for matching the CT image with the preguide library according to the embodiment of the present invention.

Reference numeral 714 of FIG. 7(*a*) refers to a preguide library. Although not separately illustrated in FIG. 7(*a*), the preguide library according to the embodiment of the present invention may include information about the shape, size, image, and material of the preguide, and about the position of a marker of a corresponding model, and reference numeral 714 refers to the shape of the preguide from among them.

Reference numeral 716 of FIG. 7(*a*) refers to a CT image with the preguide applied to the mouth. The intra-oral image obtained through the CT scanning may include information about internal tissues, such as the crown (the upper part of the tooth appearing outside the gum), the tooth root (the lower part of the tooth hidden inside the gum as the part coupled to the alveolar bone), and the alveolar bone within the oral cavity, and may include a marker image of the preguide. Since the preguide according to the embodiment of the present invention includes a marker made of a radiopaque material or a radiation semipermeable material, the implant planning system 100 may generate an image having a shape such as reference numeral 718 by matching the position of the marker recorded in the preguide library based on the marker displayed on the CT image.

According to the embodiment of the present invention, when an HU value is adjusted so that the marker of the preguide is well seen in the CT image 716, the CT image may be modified as in reference numeral 727 of FIG. 7(*b*). Then, when the practitioner selects an object corresponding to the marker 726 displayed in reference numeral 727 from the preguide library 724, the image may be matched as in reference numeral 728 based on the selected marker.

Furthermore, according to a further embodiment of the present invention, the two-dimensional CT image may be displayed at various angles as in reference numeral 729 of FIG. 7(*c*) and the image may be matched by adjusting the position of the preguide shape 730 at the corresponding angle. The image matching may be automatically performed without separate user input or may be manually performed by receiving a user input. In this case, the matching degree of the marker may be displayed in colors for every markers 731 to 736. For example, green may be displayed when the matching of a specific marker is accurate, red when the preguide is further inside with reference to the CT image, or purple when the preguide is lifted with reference to the CT image, so the user may finely adjust the position of the preguide shape 730 and the system 100 may perfectly match the preguide library with the CT image.

Meanwhile, according to the embodiment of the present invention, the marker of the preguide may be formed at positions 731 to 736 of FIG. 7(*d*), but this is merely an example. That is, the preguide device according to the embodiment of the present invention is a ready-made product produced in advance to a certain standard according to the position to be implanted and may not be limited in form as long as it includes an impression material that may be used to mold the implant placement region in a pattern form and a marker that may be displayed on the CT image. For example, the marker may be formed at the handle 740 of FIG. 7(*e*), in which case the CT image may be matched with the preguide library based on the handle.

Returning to the description of FIG. 4 again, the maxillary image and the mandibular image may be segmented in step 420.

Figure 8:
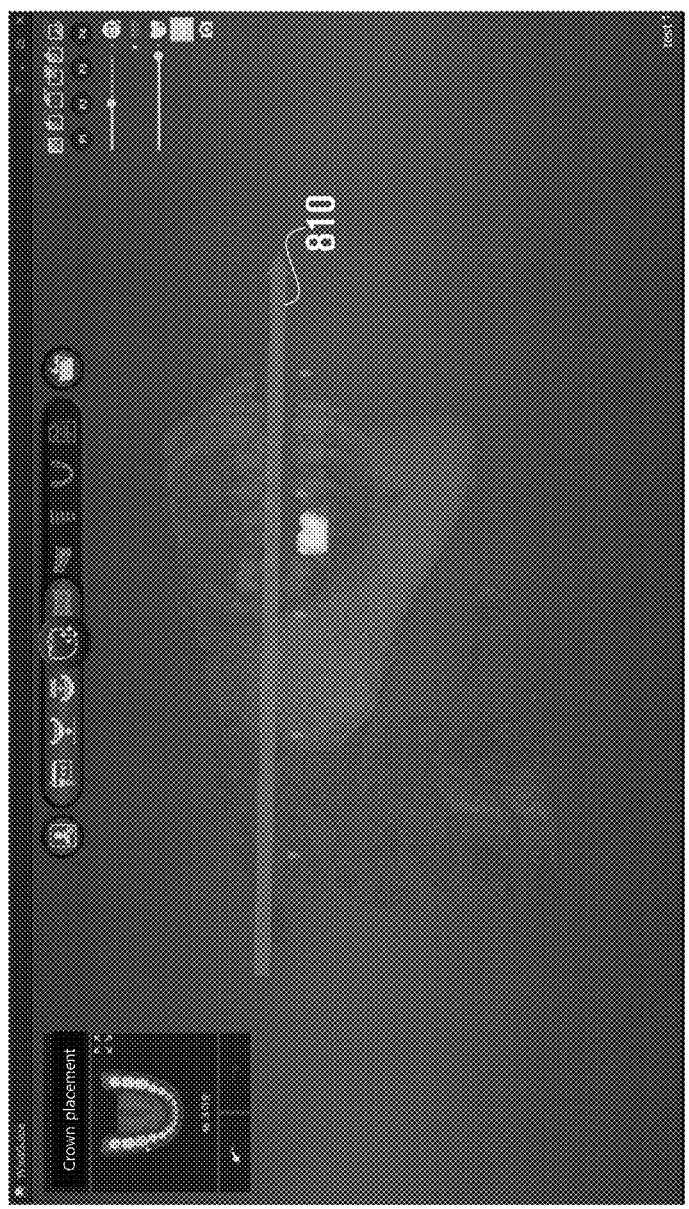
FIG. 8 is a view for explaining an example of a user interface for segmenting a maxillary image and a mandibular image in the implant planning service server according to the embodiment of the present invention.

The CT image according to the embodiment of the present invention is obtained with the maxilla and the mandibula open as much as the thickness of the preguide because it is scanned with the subject biting the preguide with his/her mouth. The system 100 according to the embodiment of the present invention may correct an error due to the thickness of the preguide by separating the maxillary image and the mandibular image based on an arbitrary line 810 as illustrated in FIG. 8 and reconstructing the separated maxillary image and mandibular image for occlusion. In this case, since the reference line 810 for separating the maxilla and the mandibula is different for each person, the system 100 according to the embodiment of the present invention may display information about the average position of the reference line and may perform correction by adjusting it by the user.

In addition, the planning system 100 according to the embodiment of the present invention may separate the maxillary image and the mandibular image in advance without receiving the user input for the reference line 810. Also, the planning system 100 may display only the maxillary image when the tooth to be treated is positioned at the maxilla, and may display only the mandibular image when the tooth is positioned at the mandibula.

Furthermore, the planning system 100 according to the embodiment of the present invention may place a crown (step 425) and set a tooth curve and a neural tube (step 430).

Figure 9:
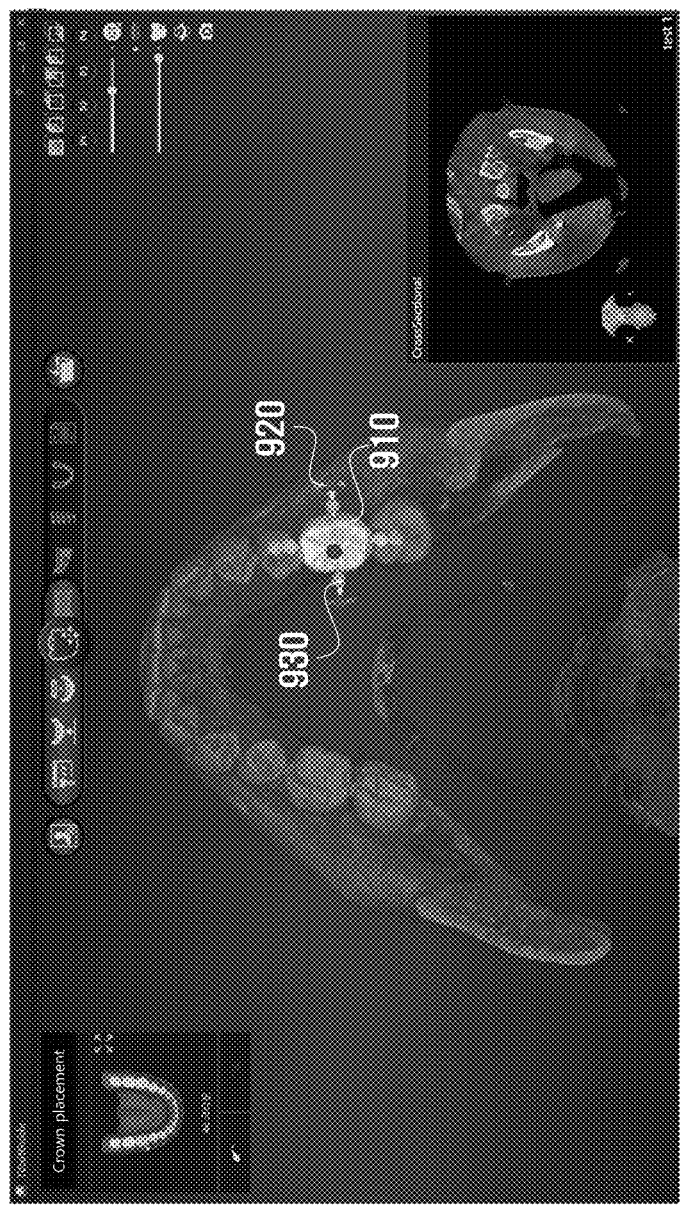
FIG. 9 is a view for explaining an example of a user interface for placing a crown at an implant placement position in the implant planning service server according to the embodiment of the present invention.

For example, the planning system 100 may provide a user interface as illustrated in FIG. 9, and the user may place a crown object 910 at the surgical position and may adjust the angle of the crown using an object 920 and the size of the crown using an object 930. In addition, the planning system 100 may provide a user interface such as reference numeral 1000 of FIG. 10 so that the user may set the tooth curve by clicking the curve in the middle part of the bone. Also, the planning system 100 may provide user interfaces such as reference numerals 1110 and 1120 of FIG. 11 so that the user may set the neural tube as in reference numeral 1130 by rotating a mouse scroll to check and select the neural tube.

Returning to the description of FIG. 3 again, the planning system may plan an implant in step 330.

Figure 12A:
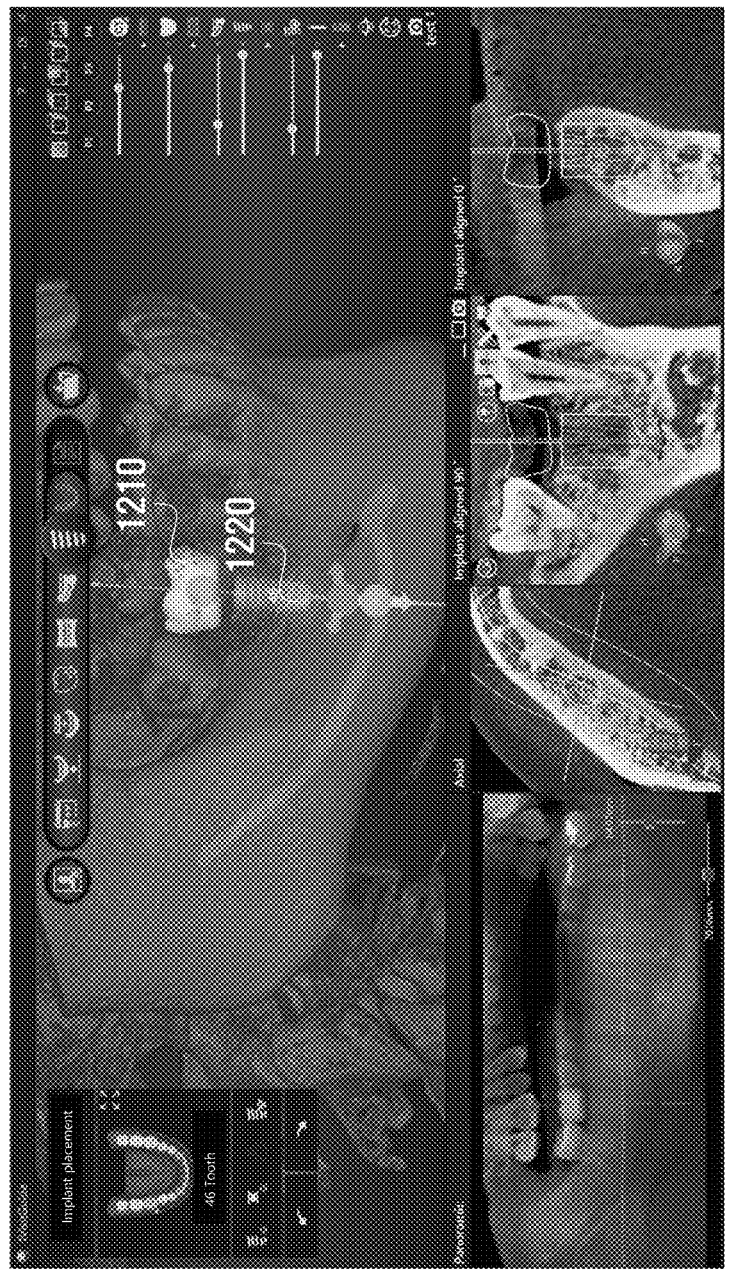
FIG. 12A is a view for explaining an example of a user interface for setting an implant type, position, depth, and angle in a CT image in the implant planning service server according to the embodiment of the present invention.

The planning system 100 may plan the implant placement by setting the position and/or direction of the implant using the oral image processed in step 320. For example, in the example of FIG. 12A, the implant planning module 133 may place a crown object 1210 at the implant placement region by setting the angle and size of the crown object in the CT image. Then, the implant planning module 133 may place an implant object 1220 at a certain distance from the placed crown object. In addition, the implant surgery may be planned by setting the size, length, position, and placement angle of the implant object.

Particularly, the planning system 100 may perform a function of providing a guide to the practitioner while placing the implant object. For example, the planning system 100 may provide a guide to position the implant at a depth of 0.5 to 1 mm from the bone, or may provide a guide to secure a distance of 2 mm or more between the implant and the root of the adjacent tooth. In addition, the planning system 100 may provide a guide to secure a distance of 3 mm or more between the implant and the nerve, or may provide a guide to secure a distance of 2 mm or more between the implant and the sinus. Furthermore, the planning system 100 may provide a guide such that the axis of the implant coincides with the center of the prosthesis, or may provide a guide to check whether the bone is sufficient at the implant placement position. As another example, the planning system 100 may provide a guide to check whether the sleeve invades the tooth or the gum. Furthermore, the planning system 100 may set an insertion direction of an implant surgical instrument, i.e., of a handpiece, as in reference numeral 1230 of FIG. 12B, together with the implant placement plan.

In step 340, the planning system 100 may generate preguide machining information in order to machine the preguide into a surgical guide for corresponding surgery according to the implant placement plan.

For example, the planning system 100 may set a guide hole region to be etched in the preguide by applying an offset in a preset range based on the type, size, and/or length of the predetermined implant sleeve. In addition, the planning system 100 may apply the insertion angle and position information of the implant surgical instrument, i.e., of the handpiece in the preguide to set a flat surface etching region at the upper portion of the preguide for the insertion of the handpiece. The generated guide machining information may be stored in an STL & XML file format (step 360).

Then, the planning system 100 may machine the preguide into the surgical guide for corresponding surgery by etching the set etching region in the preguide (step 370). More specifically, the planning system includes a milling machine, and the machining information of the preguide, i.e., the information about the guide hole region and/or the handpiece insertion region may be generated in the form of a guide machining file to be applied to the milling machine. The milling machine may machine the preguide with reference to the machining file. For example, the milling machine may generate the surgical guide for implant surgery by etching the depth and diameter region of the guide hole and the handpiece insertion region recorded in the machining file in the corresponding preguide.

Figure 13A:
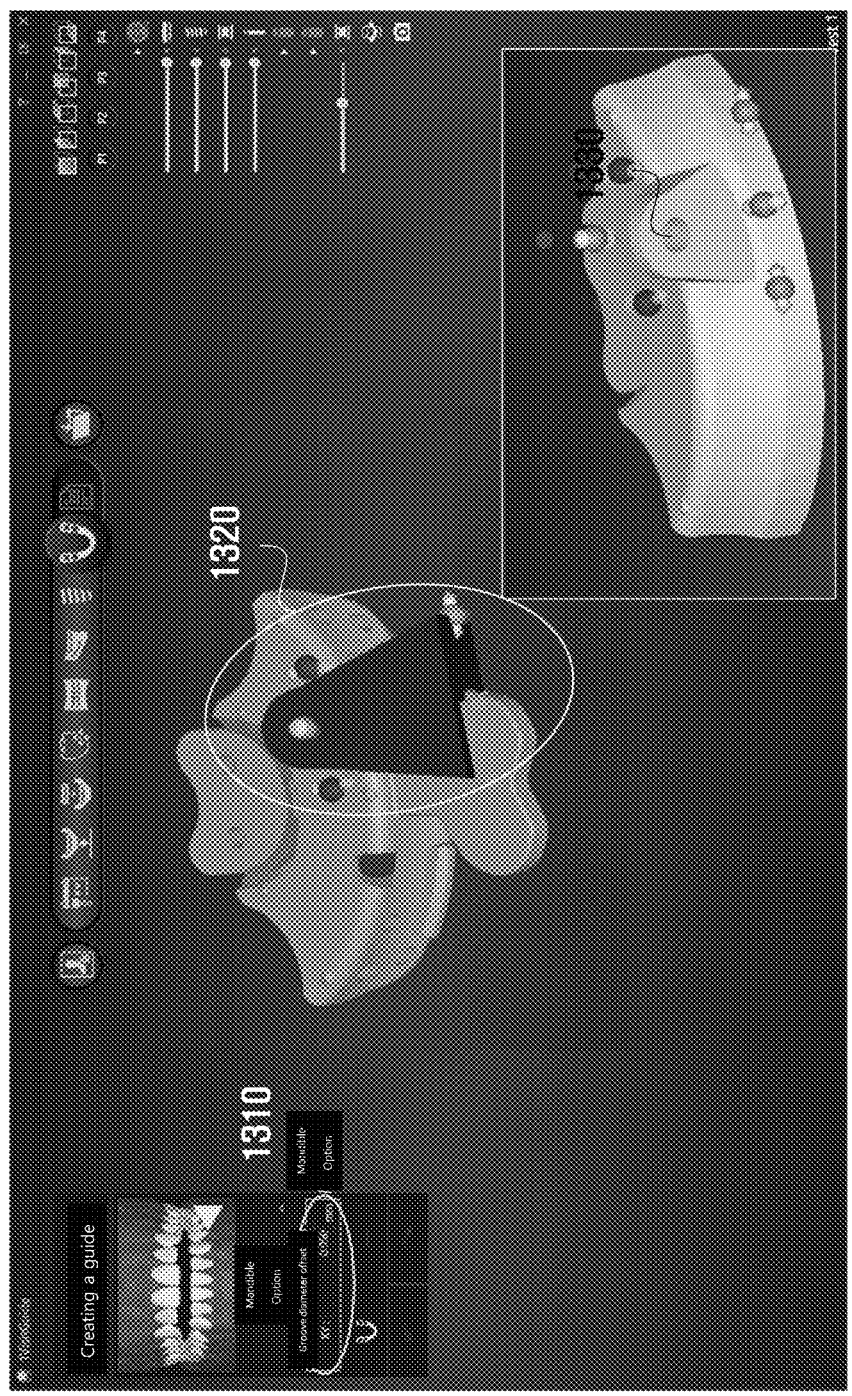
FIG. 13A is a view for explaining an example of a user interface for setting an etching region for machining the surgical guide in the implant planning service server according to the embodiment of the present invention.

For example, in the example of FIG. 13A, when the practitioner applies an offset to the predetermined implant sleeve using a menu such as reference numeral 1310, the planning system sets the guide hole etching region. When the practitioner sets a flat surface etching region using a three-dimensional user interface such as reference numeral 1320, the guide hole and the flat surface are etched in the preguide as in reference numeral 1330 and will be machined into the surgical guide for corresponding surgery.

Figure 12B:
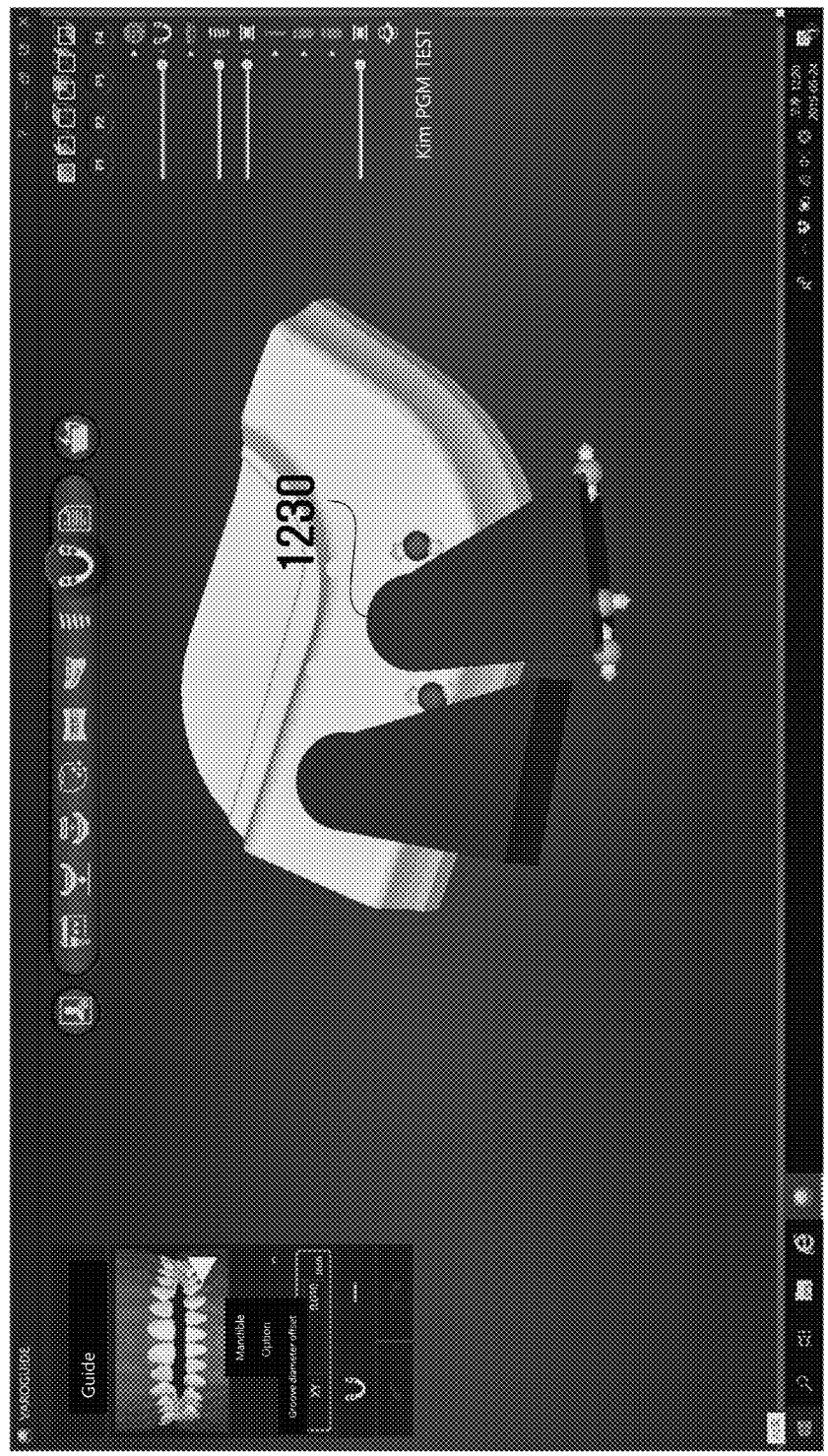
FIG. 12B is a view for explaining an example of a user interface for setting a handpiece insertion path in the implant planning service server according to the embodiment of the present invention.
Figure 13B:
FIG. 13B is a view for explaining an example of a user interface for setting an etching region for machining the surgical guide in the implant planning service server according to another embodiment of the present invention.

Meanwhile, according to a further embodiment of the present invention, a pouring hole region may be set to partially overlap with the guide hole region. The pouring hole region is a region for injecting water into the implant surgical region of the oral cavity, and may be formed to have a diameter smaller than the guide hole and may be set to partially overlap with the guide hole region. In addition, since the pouring hole diameter is less than ½ of the guide hole diameter, the guide hole region may be clearly specified even though the pouring hole region partially overlaps with the guide hole region. As another example, when the practitioner sets the insertion direction of the implant surgical instrument, i.e., of any handpiece as illustrated in FIG. 12B, an etching region for the flat surface may be set according to the insertion path of the handpiece such as reference numeral 1340 of FIG. 13B in the planning system.

Meanwhile, it may be considered that the teeth to be implanted are adjacent to each other. In this case, a first guide hole and a second guide hole are disposed adjacent to each other but do not overlap. However, a first handpiece region for the handpiece insertion path for the first guide hole may overlap with a second handpiece region for the handpiece insertion path for the second guide hole. In this case, the first handpiece region and the second handpiece region may be distinguished in a stepped manner.

In step 380 of FIG. 3, the planning system may report the surgical plan while visually providing the practitioner with information about the type, size, position, and/or direction of the CT image, crown and implant used to match the preguide. In this case, the planning system may analyze the CT image of the subject to generate information about the subject's bone density, the distance between the implant placement position and the neural tube, etc., and report the information.

Figure 5:
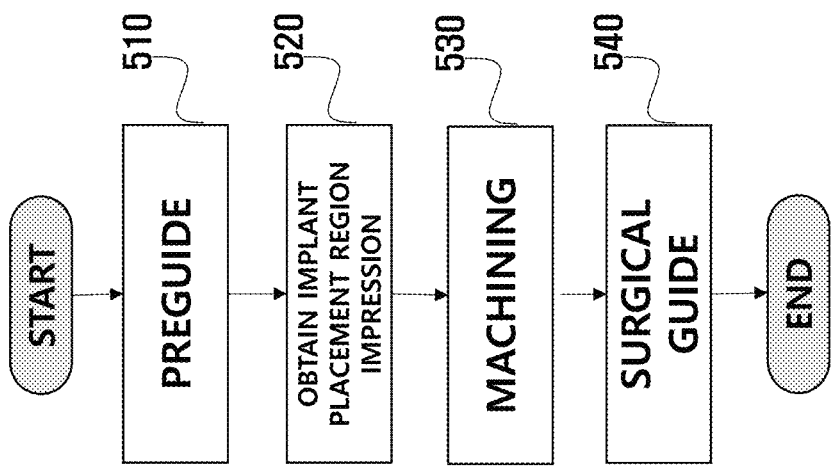
FIG. 5 is a flowchart for explaining a process of machining the preguide to generate a surgical guide for corresponding surgery according to the embodiment of the present invention.

FIG. 5 is a flowchart for explaining a series of processes in which any implant surgery is planned for the preguide according to the embodiment of the present invention and the preguide is machined into a surgical guide for the surgery.

In step 510, a preguide set produced in advance to a certain standard according to the implant placement position may be prepared. The preguide according to the embodiment of the present invention may include a maxillary (upper jaw) model and a mandibular (lower jaw) model according to the implant placement position. For example, the preguide set according to the embodiment of the present invention may be formed of at least one maxillary model and mandibular model formed to group human teeth in any range so that the teeth belong to at least one group and to cover the tooth position of the corresponding group.

The preguide according to the embodiment of the present invention may include a guide tray, an impression material such as resin formed in the guide tray to obtain an impression inside the oral cavity, and one or more markers made of a radiopaque or radiation semipermeable material.

In step 520, the practitioner obtains the impression of the implant placement region through the impression material of the preguide. That is, an arbitrary model covering a position to be implanted is applied to the mouth of the subject and an implant placement region is molded in a pattern form through the impression material. For example, when the impression material is resin, the impression material may be cured through photopolymerization.

The subject's oral pattern obtained by the preguide is intactly formed in the surgical guide that is finally completed (step 530) by machining the preguide in the milling machine (step 520) according to the embodiment of the present invention. Therefore, the subject's oral pattern may be used as a means for physically matching the surgical guide with the implant placement region of the subject. In other words, since the implant placement region is molded in the pattern form in the impression resin included in the preguide according to the embodiment of the present invention and the impression resin molded in the pattern form is then included in the surgical guide completed by machining the preguide, the preguide may function as a corresponding surgery-specific surgical guide even though the preguide is a ready-made product.

In step 530, the preguide may be machined according to the plan for implant surgery.

According to the embodiment of the present invention, the preguide is not a model produced according to the oral shape of the subject, but is produced in advance to a certain standard. Thus, the information about the standard of each model of the preguide, i.e., the information about the shape, size, image, and material of the preguide, and the position of the marker may be prestored in the service server in the form of a preguide library.

In addition, the preguide library may be matched with the CT image based on the preguide marker included in the oral CT image with the preguide applied to the mouth. The intra-oral image obtained through the CT scanning includes information about internal tissues, such as the crown (the upper part of the tooth appearing outside the gum), the tooth root (the lower part of the tooth hidden inside the gum as the part coupled to the alveolar bone), and the alveolar bone within the oral cavity, and includes the marker image of the preguide. This is because the marker is recorded in the CT image since the marker is made of a radiopaque or radiation semipermeable material in the preguide according to the embodiment of the present invention. Therefore, the marker may be identified in the CT image, and since the prestored preguide library includes marker information, the CT image and the preguide library may be matched based on the marker.

Meanwhile, the practitioner may plan the implant using the CT image matched with the preguide library. For example, the crown object may be placed at the implant placement region by setting the angle and size of the crown object in the CT image, the implant object may be placed at a certain distance from the crown object, and the implant surgery may be planned by setting the size, length, position, and placement angle of the implant object.

Then, the machining information of the preguide may be generated according to the plan for implant placement in the service server, and thus the preguide may be machined by the milling machine. For example, when the guide hole region to be etched in the preguide is set by applying an offset in a preset range based on the type, size, and/or length of the implant sleeve, and the insertion angle and position information of the implant surgical instrument, i.e., of the handpiece is applied to set the flat surface etching region at the upper portion of the preguide for the insertion of the handpiece, the preguide may be machined. Then, the machined preguide may operate as a surgical guide for corresponding surgery.

In accordance with the exemplary embodiments of the present invention, it is possible to improve the convenience of the patient and the practitioner by shortening the time for planning the implant surgery and manufacturing the guide stent. More specifically, according to the exemplary embodiments of the present invention, it is possible to shorten the preparation time for implant surgery by machining the standardized guide stent according to the surgical plant rather than manufacturing the separate guide stent for each patient. Furthermore, the guide stent according to the exemplary embodiments of the present invention can be easily and quickly manufactured and can be stably mounted into the subject's oral cavity without an error.

The embodiments disclosed in the specification and drawings are only illustrative of the present invention for the purpose of facilitating the explanation and understanding of the present invention, and are not intended to limit the scope of the present invention. It will be apparent to those skilled in the art that other modifications based on the technical idea of the present invention are possible in addition to the embodiments disclosed herein.

What is claimed is:

1. A method of supporting implant surgery in a server, comprising:
   a) obtaining a subject's oral CT image scanned with a guide model inserted into an oral cavity of the subject, the guide model being manufactured to a standard to group human teeth in any range so that the teeth belong to at least one group and to cover a tooth position of a corresponding group, the guide model comprising a marker made of a radiopaque or radiation semipermeable material;
   b) loading a library as information about the standard of the guide model, identifying the marker in the oral CT image, and generating a library matching CT image by matching the oral CT image with the library based on the marker included in the library and the marker identified in the oral CT image; and
   c) planning implant surgery of the subject using the library matching CT image;
   wherein the library comprises a database pre-stored in a storage unit, the database includes information about shape, size, image, material of the guide model, and a position of the marker of the guide model; and
   wherein the oral CT image comprises a maxillary image and a mandibular image, and the method further comprises correcting an error associated with a thickness of the guide model by separating the maxillary image and the mandibular image and reconstructing the separated maxillary image and mandibular image for occlusion.

2. The method according to claim 1, comprising, after the c) planning implant surgery of the subject, d) generating information about a machining region of the guide model to machine the guide model into a surgical guide for the implant surgery according to the plan for implant surgery of the subject;

wherein the guide model is machined into the surgical guide in a milling machine, and the guide model further comprises a jig holder configured to couple the guide model to the milling machine.

3. The method according to claim 2, wherein:

the guide model comprises an impression material for obtaining an impression within the oral cavity, and an oral pattern for an implant placement region of the subject is formed through the impression material; and the surgical guide is formed by machining the guide model and comprises the oral pattern, and the oral pattern functions as a means for physically matching the surgical guide with the implant placement region of the subject.

4. The method according to claim 3, wherein the impression material is dental photopolymerized resin or self-polymerized resin, which is polymerized in the oral cavity of the subject.

5. The method according to claim 4, wherein the guide model comprises a vinyl film formed on its one surface on which the oral pattern is formed through the impression material.

6. The method according to claim 3, wherein the d) generating information comprises setting at least one of a guide hole region of the guide model and an insertion region of a handpiece as an implant surgical instrument.

7. The method according to claim 3, wherein the c) planning implant surgery of the subject comprises:

placing a crown object at an implant placement region of the matching CT image by setting an angle and size of the crown object;

placing an implant object at a certain distance from the placed crown object; and setting at least one of an type, size, length, position, and an implantation angle of the implant object.

8. The method according to claim 7, comprising providing guide information about at least one of a position from the implant object placed on the matching CT image to a bone, a position from the implant object to a root of a tooth adjacent to the implant placement region, and a distance between the implant object and a nerve.

9. The method according to claim 8, comprising providing at least one of guide information about whether the axis of the implant object coincides with the center of a prosthesis and guide information about whether a sleeve of the implant invades the tooth or the gum.

10. The method according to claim 1, wherein the b) loading a library comprises:

setting a tooth curve in the matching CT image; and
setting a mandibular neural tube in the matching CT image.

11. The method according to claim 1, comprising, after the c) planning implant surgery of the subject, reporting information about at least one of a type, size, position, and direction of an implant used for the surgery planned using the matching CT image.

12. The method according to claim 1, comprising, after the c) planning implant surgery of the subject, reporting at least one of bone density information of the subject and information about a distance between the implant placement position and a neural tube, estimated by analyzing the oral CT image or the matching CT image.

13. A system for supporting implant surgery, comprising:

a guide model manufactured to a standard to group human teeth in any range so that the teeth belong to at least one group and to cover a tooth position of a corresponding group, the guide model comprising a marker made of a radiopaque or radiation semipermeable material;

a CT scanner for scanning a subject's oral CT image with the guide model inserted into an oral cavity of the subject;

a storage unit configured to store a library comprising a database, the database including information about shape, size, image, material of the guide model, and a position of the marker of the guide model; and a server configured to load a library as information about the standard of the guide model, to identify the marker in the oral CT image, to generate a library matching CT image by matching the oral CT image with the library based on the marker included in the library and the marker identified in the oral CT image, and to plan implant surgery of the subject using the library matching CT image, wherein the oral CT image comprises a maxillary image and a mandibular image, and the server is further configured to correct an error associated with a thickness of the guide model by separating the maxillary image and the mandibular image and reconstructing the separated maxillary image and mandibular image for occlusion; and wherein the guide model further comprises a maxillary model and a mandibular model, the maxillary model is configured to cover a portion of maxillary teeth, and the mandibular model is configured to cover a portion of mandibular teeth.

14. The system according to claim 13, wherein the server sets information about a machining region of the guide model to machine the guide model into a surgical guide for the implant surgery according to the plan for implant surgery of the subject;

wherein the guide model is machined into the surgical guide in a milling machine, and the guide model further comprises a jig holder configured to couple the guide model to the milling machine.

15. The system according to claim 14, wherein the milling machine is configured for machining the guide model into the surgical guide by etching the machining region in the guide model according to the information about the machining region of the guide model.

16. The system according to claim 13, wherein:

the guide model comprises an impression material for obtaining an impression within the oral cavity, and an oral pattern for an implant placement region of the subject is formed through the impression material; and the surgical guide is formed by machining the guide model and comprises the oral pattern, and the oral pattern functions as a means for physically matching the surgical guide with the implant placement region of the subject.

17. The system according to claim 16, wherein the guide model comprises the impression material that is dental photopolymerized resin or self-polymerized resin polymerized in the oral cavity of the subject.

18. The system according to claim 16, wherein the guide model comprises a vinyl film formed on its one surface on which the oral pattern is formed through the impression material.

19. A server for supporting implant surgery, comprising:

a storage unit configured to store a library as information about the standard of a guide model, the guide model being manufactured to a standard to group human teeth in any range so that the teeth belong to at least one group and to cover a tooth position of a corresponding group, the guide model comprising a marker made of a radiopaque or radiation semipermeable material, the library comprising a database including information about shape, size, image, material of the guide model, and a position of the marker of the guide model;

an image processing module configured to identify the marker of the guide model in a subject's oral CT image scanned with the guide model inserted into an oral cavity of the subject and to generate a library matching CT image by matching the oral CT image with the library based on the marker included in the library and the marker identified in the oral CT image, wherein the oral CT image comprises a maxillary image and a mandibular image, and the image processing module is further configured to correct an error associated with a thickness of the guide model by separating the maxillary image and the mandibular image and reconstructing the separated maxillary image and mandibular image for occlusion; and an implant planning module configured to plan implant surgery of the subject using the library matching CT image.

20. The server according to claim 19, comprising a guide design module configured to set a machining region of the guide model and generate a machining file of the guide model in order to machine the guide model into a surgical guide for the implant surgery according to the plan for implant surgery of the subject;

wherein the guide model is machined into the surgical guide in a milling machine, and the guide model further comprises a jig holder configured to couple the guide model to the milling machine.

21. The server according to claim 20, wherein the guide model sets at least one of a guide hole region of the guide model and an insertion region of a handpiece as an implant surgical instrument.

22. The server according to claim 19, comprising a file management module configured to perform a function of converting the oral CT image, implant planning information using the matching CT image, and a machining file of the guide file in a predetermined format.

23. The server according to claim 19, wherein the machining file comprises information about an etching depth of a guide hole.

24. The server according to claim 23, wherein the image processing module sets a tooth curve and a mandibular neural tube in the matching CT image.

25. The server according to claim 19, wherein the implant planning module places a crown object at an implant placement region of the matching CT image by setting an angle and size of the crown object, places an implant object at a certain distance from the placed crown object, and sets at least one of an type, size, length, position, and an implantation angle of the implant object.

26. A non-transitory computer readable medium configured to perform a function of supporting implant surgery in a server, performing:

a function of obtaining a subject's oral CT image scanned with a guide model inserted into an oral cavity of the subject, the guide model being manufactured to a standard to group human teeth in any range so that the teeth belong to at least one group and to cover a tooth position of a corresponding group, the guide model comprising a marker made of a radiopaque or radiation semipermeable material;

a function of loading a library as information about the standard of the guide model, identifying the marker in the oral CT image, and generating a library matching CT image by matching the oral CT image with the library based on the marker included in the library and the marker identified in the oral CT image; and a function of planning implant surgery of the subject using the library matching CT image;

wherein the library comprises a database pre-stored in a storage unit, the database includes information about shape, size, image, material of the guide model, and a position of the marker of the guide model; and wherein the oral CT image comprises a maxillary image and a mandibular image, and the non-transitory computer readable medium is further configured to perform a function of correcting an error associated with a thickness of the guide model by separating the maxillary image and the mandibular image and reconstructing the separated maxillary image and mandibular image for occlusion.

27. The non-transitory computer readable medium according to claim 26, performing a function of setting a machining region of the guide model to machine the guide model into a surgical guide for the implant surgery according to the plan for implant surgery of the subject;

wherein the guide model is machined into the surgical guide in a milling machine, and the guide model further comprises a jig holder configured to couple the guide model to the milling machine.

28. The non-transitory computer readable medium according to claim 27, performing:

a function of setting a tooth curve in the matching CT image;

a function of setting a mandibular neural tube in the matching CT image; and a function of setting at least one of a guide hole region of the guide model and an insertion region of a handpiece as an implant surgical instrument.

* * * * *